United States Patent
Gomes et al.

(10) Patent No.: US 11,156,601 B2
(45) Date of Patent: Oct. 26, 2021

(54) IN VITRO NEONATAL BIOMIMETIC (NMIMIC) MODEL AND METHODS OF USING SAME

(71) Applicant: Sanofi Pasteur VaxDesign Corporation, Orlando, FL (US)

(72) Inventors: Evan Gomes, Orlando, FL (US); Tirumalai Kamala, Orlando, FL (US); Luis Mosquera, Orlando, FL (US); Vaughan Wittman, Napa, CA (US); William Warren, Orlando, FL (US); Janice Moser, Orlando, FL (US); Donald Drake, Orlando, FL (US)

(73) Assignee: SANOFI PASTEUR VAXDESIGN CORPORATION, Orlando, FL (US)

( * ) Notice: Subject to any disclaimer, the term of this patent is extended or adjusted under 35 U.S.C. 154(b) by 131 days.

(21) Appl. No.: 16/330,152

(22) PCT Filed: Sep. 7, 2017

(86) PCT No.: PCT/US2017/050408
§ 371 (c)(1),
(2) Date: Mar. 4, 2019

(87) PCT Pub. No.: WO2018/048988
PCT Pub. Date: Mar. 15, 2018

(65) Prior Publication Data
US 2019/0187127 A1  Jun. 20, 2019

Related U.S. Application Data

(60) Provisional application No. 62/384,897, filed on Sep. 8, 2016.

(51) Int. Cl.
*G01N 33/50* (2006.01)
*C12N 5/0781* (2010.01)
*C12N 5/0783* (2010.01)
*C12N 5/0784* (2010.01)

(52) U.S. Cl.
CPC ......... *G01N 33/505* (2013.01); *C12N 5/0635* (2013.01); *C12N 5/0636* (2013.01); *C12N 5/0639* (2013.01); *G01N 33/5052* (2013.01); *G01N 33/5088* (2013.01); *C12N 2500/92* (2013.01); *C12N 2500/99* (2013.01); *C12N 2501/21* (2013.01); *C12N 2501/2306* (2013.01); *C12N 2501/2312* (2013.01); *C12N 2501/2321* (2013.01); *C12N 2501/51* (2013.01); *C12N 2502/1107* (2013.01); *C12N 2502/1114* (2013.01); *C12N 2502/1121* (2013.01); *C12N 2533/50* (2013.01)

(58) Field of Classification Search
None
See application file for complete search history.

(56) References Cited

U.S. PATENT DOCUMENTS

2009/0117581 A1  5/2009  Warren et al.

FOREIGN PATENT DOCUMENTS

| WO | 2007/076061 | 7/2007 |
| WO | 2013/134464 | 9/2013 |

OTHER PUBLICATIONS

Aljurayyan et al, May 2016, Antiviral Res. vol. 132: 122-130.*
Perez-Anders et al., 2010, Cytometry vol. 78B: S47-S60.*
Ma et al., 2009, Imm. Cell. Biol. vol. 87: 590-600.*
International Search Report and Written Opinion of the International Searching Authority, dated Oct. 30, 2017 in corresponding International Patent Application No. PCT/US2017/050408.
Higbee et al., "An Immunologic Model for Rapid Vaccine Assessment—A clinical Trial in a Test Tube", Atla. Alternatives to Laboratory Ani, 37(1): 19-27 (2009).
Drake et al., "In Vitro Biomimetic Model of the Human Immune System for Predictive Vaccine Assessments", Disruptive Science and Technology, 1(1): 28-40 (2012).
Basha et al., "Immune responses in neonates", Expert Review of Clinical Immunology, 10(9): 1171-1184 (2014).

* cited by examiner

Primary Examiner — Amy E Juedes
(74) Attorney, Agent, or Firm — Wenderoth, Lind & Ponack, L.L.P.

(57) ABSTRACT

In vitro biomimetic models of the neonatal immune system are provided along with methods of using the models in pre-clinical assessment of infant immune cell-mediated and humoral responses to immunogenic stimulation, such as vaccination. The models include one comprising cord blood-derived T follicular helper cells and B cells, and one comprising cord blood-derived dendritic cells and CD4+ T cells. The models can be used, for example, to assess candidate vaccines via analysis of cellular responses to antigen and vaccine exposure.

24 Claims, 14 Drawing Sheets

IN VITRO NEONATAL BIOMIMETIC (NMIMIC) MODEL AND METHODS OF USING SAME

BACKGROUND OF INVENTION

Vaccination is the best defense against infection, and the first few months of life provide an important period in which vaccines can induce robust protection against disease. However, the clinical development and improvement of vaccines and immunotherapies is stymied by the lack of appropriate in vitro assays for testing immune responses in immature immune systems. Development of in vitro models of neonatal and infant immunity would be of great benefit in advancing research into vaccines that can be administered following birth. The invention described herein is directed to this and other important goals.

BRIEF SUMMARY OF INVENTION

Provided herein are cell culture constructs and methodologies that together serve as in vitro models of the mammalian neonatal immune system. These mammalian umbilical cord blood-based neonatal modular immune in vitro construct (nMIMIC) models can be used to predict early life immune responses to selected antigens and can serve as primary screens in the pre-clinical evaluation of infant and toddler vaccines.

The nMIMIC models of the invention recapitulate aspects of early life naïve immunity. Using nascent cord blood-derived immunocytes in the nMIMIC models, the models disclosed herein emulate the immune response of neonates and infants observed in the clinic. These nMIMIC models offer the ability to utilize components of the mammalian neonatal immune system (e.g., T, B, and dendritic cells (DCs)) from cord blood and present them in culture at ratios similar to that observed at physiological concentrations in vivo. With these models, the inventors have been able to (1) apply antigen-heated, cord blood derived-DCs to CD4+ T cells to generate cell-mediated responses, and (2) differentiate cord blood CD4+ T cells into a specialized class of T lymphocytes, T follicular helper cells ($T_{FH}$). which are essential for B cell help and the humoral response, and apply these $T_{FH}$ cells to naïve B cells to generate antigen-specific antibody responses to childhood vaccines.

Embodiments of the present invention include two particular nMIMIC models, the nMIMIC DC/T cell model and the nMIMIC B cell/$T_{FH}$ cell model, and methods of using these models to provide information about cellular responses of components of the mammalian neonatal immune system to antigens, and in assessing candidate vaccines.

nMIMIC DC/T Cell Model

The nMIMIC DC/T cell model primarily comprises cord-blood derived dendritic cells (DCs) and cord blood CD4+ T cells, and it can be used, for example, to assay the effects of selected agents on neonatal antigen presentation and CD4+ T cell response. While it will be readily apparent that the nMIMIC DC/T cell model can be used in a number of different manners, in a non-limiting example this model can be exemplified as an in vitro method of assessing the response of cells of the neonatal immune system to a selected agent. In particular, and in a first embodiment, the present invention is directed to a method of assessing a cellular response to a selected agent comprising:
 (a) adding the selected agent to a first in vitro cell culture comprising cord blood-derived dendritic cells (DCs) and maintaining the cell culture under conditions promoting uptake of the selected agent by the DCs to form a first population of primed DCs,
 (b) forming a second in vitro cell culture comprising primed DCs developed in (a) and cord blood CD4+ T cells and maintaining the cell culture under conditions promoting T cell activation,
 (c) adding a second population of primed DCs to the cell culture of (b) and maintaining the culture under conditions promoting a T cell response, wherein the second population of primed DCs is prepared in the same manner as the first population of primed DCs, and
 (d) analyzing supernatant and/or T cells from the cell culture of (c) for a T cell response, thereby assessing the cellular response to a selected agent.

In another non-limiting example, the nMIMIC DC/T cell model can be exemplified as an in vitro method of screening selected agents (e.g., antigen, vaccine) for their activity on components of the mammalian neonatal immune system. In particular, and in a second embodiment, the present invention is directed to a method of screening a selected agent for activity comprising:
 (a) adding the selected agent to a first in vitro cell culture comprising cord blood-derived dendritic cells (DCs) and maintaining the cell culture under conditions promoting the selected agent uptake by the DCs to form a first population of primed DC's,
 (b) forming a second in vitro cell culture comprising primed Des developed in (a) and cord blood CD4+ T cells and maintaining the cell culture wider conditions promoting T cell activation,
 (c) adding a second population of primed DCs to the cell culture of (b) and maintaining the culture under conditions promoting a T cell response, wherein the second population of primed Des is prepared in the same manner as the first population of primed DCs, and
 (d) analyzing supernatant and/or T cells from the cell culture of (c) for a T cell response, thereby screening the selected agent for activity.

In aspects of these first and second embodiments, the first cell culture is maintained fora period of about 3, 6, 9, 12, 15, 18, 21, 24, 27, 30, 33, 36, 39, 42, 45, 48 or more hours prior to formation of the second cell culture. In a particular aspect, the first cell culture is maintained for a period of about 12-36 hours prior to formation of the second cell culture.

In aspects of these first and second embodiments, the second cell culture is maintained fora period of about 1, 2, 3, 4, 5, 6, 7, 8.9, 10, 11, 12, 13, 14, 15, 16, 17, 18, 19, 20 or more days prior to adding the second population of primed DCs. In a particular aspect, the second cell culture is maintained for a period of about 5-10 days prior to adding the second population of primed DCs.

In aspects of these first and second embodiments, the culture of (c) is maintained for a period of about 1, 2, 3, 4, 5, 6, 7, 8, 9, 10, 11, 12 or more hours prior to the analyzing of (d). In a particular aspect, the culture of (c) is maintained for a period of about 2-8 hours prior to the analyzing of (d).

In aspects of these first and second embodiments, the T cell response may be production of a cytokine or a marker. Exemplary cytokines include, but are not limited to, one or more of TNFα, IFNγ, IL-2, IL-4, IL-6, IL-8, IL-9, IL-10, IL-13, IL-17A, IL-17F, IL-18, IL-21, IL-22, and IL-26. Exemplary markers include, but are not limited to, one or more of CD25, CD26, CD27, CD28, CD30, CD44, CD69, CD71, CD134, and CD154.

In aspects of these first, and second embodiments, the selected agent, may be an antigen, vaccine, protein, peptide, polynucleotide, oligonucleotide, polysaccharide, virus, virion, bacteria, fungi, and fragments thereof.

In aspects of these first and second embodiments, the cord blood T cells are autologous to the cord blood-derived DCs (i.e., from the same organism). In other aspects of this embodiment, the cord blood T cells are allogeneic to the cord blood-derived Des (i.e., from another organism of the same species).

In aspects of these first and second embodiments, the ratio of primed DC's to cord blood T cells in the culture of (b) ranges from about 1:5 to about 1:100.

In aspects of these first and second embodiments, the ratio of the second population of primed DCs added to the culture of (c) to cord blood T cells ranges from about 1:5 to about 1:100.

In aspects of these first and second embodiments, the cord blood-derived Des may be, characterized as expressing one or more of the following markers; CD14, CDI6, CD25, CD80, CD86, and HLA-DR.

In another aspect of the invention and of these first and second embodiments, the cord blood-derived DCs may be prepared by a method comprising:
(a) culturing endothelial cells on an upper surface of a porous membrane, wherein said porous membrane is housed in an upper chamber of a cell culture well that is suspended over, and is separable from, a lower chamber of the well;
(b) applying cord blood mononuclear cells (CBMCs) to the endothelial cells the porous membrane of (a);
(c) removing the upper chamber housing the porous membrane and endothelial cells from the well about 48 hours after application of the CBMCs; and
(d) isolating dendritic cells from the lower chamber of the well.

In the methods of preparing the cord blood-derived DC's, the porous membrane may be a polycarbonate membrane, have pores ranging size from about 1 to 15 μm in diameter, or both. A permeable support may be used, in some embodiments, to provide the upper chamber of the well, the polycarbonate membrane, and the lower chamber of the well. An example of such a permeable support is the Coming Inc. Transwell® permeable supports.

In the methods of preparing the cord blood-derived DCs, the lower chamber of the well may comprise extracellular matrix (ECM) material. In some embodiments, the ECM material may comprise a material selected from, but not limited to, gelatin, collagen, synthetic ECM materials, poly (lactic-co-glycolic acid) (PLGA), polyglycolic acid (PGA), natural ECM materials, chitosan protosan, fibronectin, vitronectin, collagen I, collagen IV, laminin, and mixtures thereof. The lower chamber of the well may further comprise one of more of fibroblasts, support cells, and stromal cells.

In the methods of preparing the cord blood-derived DCs, the endothelial cells may be, but are not limited to, human umbilical vein endothelial cells (HUVECs) and the human somatic cell hybrid EA.hy926. In additional aspects, the endothelial cells may be a transformed endothelial cell line.

In the methods of preparing the cord blood-derived DCs, the endothelial cells may be cultured on the both sides of the porous membrane.

In the methods of preparing the cord blood-derived DCs, the endothelial cells may be cultured to confluency prior to adding the CBMCs.

In the methods of preparing the cord blood-derived DCs, the endothelial cells may be cultured until multilayer cell growth is achieved and prior to adding the CBMCs.

In the methods of preparing the cord blood-derived DCs, a layer of ECM material may be on the upper surface of the porous membrane and the endothelial cells are cultured on the ECM material layer. Alternatively, a layer of ECM material may be on the upper surface and the lower surface of the porous membrane and the endothelial cells are cultured on both layers of ECM material. The ECM material may comprise a material selected from, but not limited to, gelatin, collagen, synthetic ECM materials, PLGA, PGA, natural ECM materials, chitosan, protosan, fibronectin, vitronectin, collagen I, collagen IV, laminin, and mixtures thereof In aspects of these embodiments, the lower chamber of the well that is used to prepared the dendritic cells may also serve as the first cell culture of (a).

nMIMIC B cell/$T_{FH}$ Cell Model

The nMIMIC B cell/$T_{FH}$ cell model primarily comprises cord-blood derived T follicular helper ($T_{FH}$) cells and cord blood B cells, and it can be used, for example, to assay the effects of selected agents on antigen presentation and B cell response. The nMIMIC B cell/$T_{FH}$ cell model can be used in a number of different manners, including as a non-limiting example an in vitro method of assessing the response of cells of the neonatal immune system to a selected vaccine. Thus, and in a third embodiment, the present invention is directed to a method of screening a vaccine for activity comprising:
(a) adding a vaccine and one or more cellular activator to a first in vitro cell culture comprising cord blood CD4+ T cells and maintaining the cell culture under conditions promoting development of vaccine-specific T follicular helper ($T_{FH}$) cells,
(b) forming a second in vitro cell culture comprising $T_{FH}$ cells developed in (a) and cord blood B cells,
(c) adding a vaccine-specific antigen to the cell culture of (b) and maintaining the culture under conditions promoting a cellular response, and
(d) analyzing supernatant and/or cells from the cell culture of (c) for a cellular response, thereby screening a vaccine for activity.

In another non-limiting example, the nMIMIC B cell/$T_{FH}$ cell model can be exemplified as an in vitro method of assessing the potential efficacy of a vaccine via in vitro testing. In particular, and in a fourth embodiment, the present invention is directed to a method of assessing efficacy of a vaccine comprising:
(a) adding a vaccine and one or more cellular activator to a first in vitro cell culture comprising cord blood CD4+ T cells and maintaining the cell culture under conditions, promoting development of vaccine-specific T follicular helper ($T_{FH}$) cells,
(b) forming a second in vitro cell culture comprising $T_{FH}$ cells developed in(a) and cord blood B cells,
(c) adding a vaccine-specific antigen to the cell culture of (b) and maintaining the culture under conditions promoting a cellular response, and
(d) analyzing supernatant and/or cells from the cell culture of (c) for a cellular response, thereby assessing efficacy of a vaccine.

In a further non-limiting example, the nMIMIC B cell/$T_{FH}$ cell model can be exemplified as an in vitro method of predicting in vivo efficacy of a vaccine using an in vitro cell culture. In particular, and in a fifth embodiment, the present invention is directed to a method of predicting in vivo efficacy of a vaccine using an in vitro cell culture comprising:
(a) adding a vaccine and one or more cellular activator to a first cell, culture comprising cord blood CD4+ T cells and maintaining the cell culture under conditions promoting development of vaccine-specific T follicular helper ($T_{FH}$) cells, (b) funning a second cell culture comprising $T_{FH}$ cells developed in (a) and cord blood B cells, (c) adding a vaccine-specific antigen to the cell culture of (b) and maintaining the culture under conditions promoting a cellular response, and (d) analyzing supernatant and/or cells from the cell culture of (c) for a cellular response, wherein when a cellular response is found the vaccine is predicted to have in vivo efficacy.

In aspects of these third, fourth and fifth embodiments, the first cell culture is maintained for a period of about 3, 4, 5, 6, 7, 8, 9, 10, 11. 12, 13, 14, 15 or more days. In a particular aspect, the first cell culture is maintained for a period of about 8-12 days.

In aspects of these third, fourth and fifth embodiments, additional vaccine is added to the first cell culture at least once, twice, thrice, or more. In a particular aspect, the additional vaccine is added to the first cell culture at least once. Irradiated feeder cells may be added to the first culture upon one or more of the repetitions of vaccine addition. The irradiated feeder cells may be, but are not limited to, cord blood mononuclear cells (CBMCs) grown in a serum-free culture media.

In aspects of these third, fourth and fifth embodiments, the first cell culture is maintained for a period of about 3, 4, 5, 6, 7, 8, 9, 10, 11, 12, 13, 14, 15 or more days, additional vaccine is added on day 2, 3 or 4 after the initial vaccine addition, and additional vaccine is added on day 5, 6 or 7 after the initial vaccine addition. In a particular aspect, the first cell culture is maintained for a period of about 8-12 days and additional vaccine is added on one of day 2, 3 or 4, and added on one of day 5, 6 or 7 after the initial vaccine addition. Irradiated feeder cells may be added to the first culture upon repetition of one or more of the vaccine additions. The irradiated feeder cells may be, but are not limited to, cord blood mononuclear cells (CBMCs) grown in a serum-free culture media.

In aspects of these third, fourth and fifth embodiments, the vaccine-specific antigen added in (c) is added to the second cell culture of (b) shortly after the second cell culture is prepared, i.e. within about one hour after preparation of the second cell culture of (b).

In aspects of these embodiments, the culture of (c) is maintained for a period of about 5, 6, 7.8, 9, 10, 11, 12, 13. 14, 15, 16, 17, 18, 19, 20 or more days. In a particular aspect, the culture of (c) is maintained for a period of about 8-12 days.

In aspects of these third, fourth and fifth embodiments, IL-21 may be added to the culture of (c), typically at a concentration ranging from about 10 to 500 ng/ml, When added. IL-21 is added at one or more of the following time points: (i) when the vaccine-specific antigen is added to the second cell culture of (b), (ii) on day 2, 3 or 4 after preparation of the second cell culture, and (iii) on day 5, 6 or 7 after preparation of the second cell culture.

In aspects of these third, fourth and fifth embodiments, the culture of (c) is maintained for a period of about 5, 6, 7, 8, 9, 10, 11, 12, 13, 14, 15 or more days, IL-21 is added (i) when the vaccine-specific antigen is added to the second cell culture of (b), (ii) on day 2, 3 or 4 after preparation of the second cell culture, and (iii) on day 5, 6 or 7 after preparation of the second cell culture.

In aspects of these third, fourth and fifth embodiments, the cellular response is one or more of production of a cytokine by the $T_{FH}$ cells, expression of a marker by the $T_{FH}$ production of a cytokine by the B cells, expression of a marker by the B cells, and production of an antibody with binding specificity for the vaccine-specific antigen by the B cells. The cytokine may be, but is not limited to, is one or more of CXCL13, TNFα, IFNγ, IL-2, IL-4, IL-6, IL-8, IL-10, IL-13, IL-17, and IL-21. The marker may be, but is not limited to, is one or more of CD10, CD19, CD20, CD24, CD27, CD38, CD40, CD86, CD138, IgD, IgG, and IgM.

In aspects of these third, fourth and fifth embodiments, the vaccine may be, but is not limited to, an inactivated, attenuated, toxoid, subunit, conjugate, valence and heterotypic vaccine, or a protein, peptide, polynucleotide, oligonucleotide, polysaccharide, virus, virion, bacteria, fungi, or fragment thereof, or antigen-primed DCs.

In aspects of these third, fourth and fifth embodiments, the vaccine-specific antigen may be, but is not limited to, a portion of the vaccine or a component of the vaccine.

In aspects of these third, fourth and fifth embodiments, the one or more cellular activator may be, but is not limited to, anti-CD28 antibody, IL-2, IL-6, IL-12, IL-21, and IL-23.

In aspects of these third, fourth and fifth embodiments, the cord blood B cells are autologous to the cord blood CD4+ T cells (i.e., from the same organism).

In aspects of these third, fourth and fifth embodiments, the cord blood B cells may be treated with CpG2006 prior to addition of the cord blood B cells to the second cell culture.

In aspects of these third, fourth and fifth embodiments, the ratio of $T_{FH}$ cells to cord blood B cells in the second cell culture ranges from about 1:1 to about 1:100.

In aspects of these third, fourth and fifth embodiments, the second cell culture may be formed in a three-dimensional matrix. The matrix may be a gel matrix.

In another non-limiting example, the nMIMIC B cell/$T_{FH}$ cell model can be used in in vitro methods of assessing the immunogenicity of an antigen. in particular, and in a sixth embodiment, the present invention is directed to a method of assessing immunogenicity of an antigen comprising:

(a) adding an antigen and one or more cellular activator to a first in vitro cell culture comprising cord blood CD4+ T cells and maintaining the cell culture under conditions promoting development of antigen-specific T follicular helper ($T_{FH}$) cells, (b) forming a second in vitro cell culture comprising $T_{FH}$ cells developed in (a) and cord blood B cells, (c) adding the antigen to the cell culture of (b) and maintaining the culture under conditions promoting a cellular response, and (d) analyzing supernatant and/or cells from the cell culture of (c) for a cellular response, thereby assessing immunogenicity of an antigen.

In aspects of this sixth embodiment, the first cell culture is maintained for a period of about 3, 4, 5, 6, 7, 8, 9, 10, 11, 12, 13, 14, 15 or more days. In a particular aspect, the first cell culture is maintained for a period of about 8-12 days.

In aspects of this sixth embodiment, additional antigen is added to the first cell culture at least once, twice, thrice, or more. In a particular aspect, the additional antigen is added to the first cell culture at least once. Irradiated feeder cells may be added to the first culture upon one or more of the repetitions of antigen addition. The irradiated feeder cells may be, but are not limited to, cord blood mononuclear cells (CBMCs) grown in a serum-free culture media.

In aspects of this sixth embodiment, the first cell culture is maintained for a period of about 3, 4, 5, 6, 7, 8, 9, 10, 11, 12, 13, 14, 15 or more days, additional antigen is added on day 2, 3 or 4 after the initial antigen addition, and additional antigen is added on day 5, 6 or 7 after the initial antigen addition. In a particular aspect, the first cell culture is maintained for a period of about 8-12 days and additional antigen is added on one of day 2, 3 or 4, and added on one of day 5, 6 or 7 after the initial antigen addition. Irradiated feeder cells may be added to the first culture upon repetition of one or more of the antigen additions. The irradiated feeder cells may be, but are, not limited to, cord blood mononuclear cells (CBMCs) grown in a serum-free culture media.

In aspects of this sixth embodiment, the antigen added in (c) is added to the second cell culture of (b) shortly after the second cell culture is prepared, i.e. within about one hour after preparation of the second cell culture of (b).

In aspects of this sixth embodiment, the culture of (c) is maintained for a period of about 5, 6, 7, 8, 9, 10, 11, 12, 13, 14, 15, 16, 17, 18, 19, 20, 21, 22, 23, 24, 25 or more days. In a particular aspect, the culture of (c) is maintained for a'period of about 1-25 days, In aspects of this sixth embodiment, IL-21 may be added to the culture of (c), typically at a concentration ranging from about 1 to 500 ng/ml. When added, IL-21 is, added at one or more of the following time points: (i) when the antigen is added to the second cell culture of (b), (ii) on day 2, 3 or 4 after preparation of the second cell culture, and (iii) on day 5, 6 or 7 after preparation of the second cell culture.

In aspects of this sixth embodiment, the culture of (c) is maintained for a period of about 5, 6, 7, 8, 9, 10, 11, 12, 13, 14, 15 or more days, IL-21 is added (i) when the antigen is added to the second cell culture of (b), (ii) on day 2, 3 or 4 after preparation of the second cell culture, and (iii) on day 5, 6 or 7 after preparation of the second cell culture.

In aspects of this sixth embodiment, the cellular response is one or more of production of a cytokine by the $T_{FH}$ cells, expression of a marker by the T cells, production of a cytokine by the B cells, expression of a marker by the B cells, and production of an antibody with binding specificity for the antigen by the B cells. The cytokine may be, but is not limited to, is one or more of CXCL13, TNFα, IFNγ, IL-2, IL-4, IL-6, IL-8, IL-10, IL-13, IL-17, and IL-21. The marker may be, but is not limited to, is one or more of CD10, CD19CD20, CD24, CD27, CD38, CD40, CD86, CD138, IgD, IgG, and IgM.

In aspects of this sixth embodiment, the one or more cellular activator may be, but is not limited to, anti-CD28 antibody, IL-2, IL-6, IL-12, IL-21, and IL-23.

In aspects of this sixth embodiment, the cord blood B cells are autologous to the cord blood CD4+ T cells (i.e., from the same organism).

In aspects of this sixth embodiment, the cord blood B cells may be treated with CpG2006 prior to addition of the cord blood B cells to the second cell culture.

In aspects of this sixth embodiment, the ratio of $T_{FH}$ cells to cord blood B cells in the second cell culture ranges from about 1:1 to about 1:100, In a particular aspect, the ratio of $T_{FH}$ cells to cord blood B cells in the second cell culture is about 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100.

In aspects of this sixth embodiment, the second cell culture may be formed in a three-dimensional matrix. The matrix may be a gel matrix.

In a particular example, and in a seventh embodiment, the present invention is directed to a method of screening a vaccine for activity in vitro comprising:

(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 or 4 after the initial vaccine addition, and on one of day 5, 6 or 7 after the initial vaccine addition;

(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;

(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and (d) analyzing supernatant and/or cells from the cell culture of (c) for production of an antibody with binding specificity for the vaccine-specific antigen by the B cells, thereby screening a vaccine for activity in vitro.

In another example, and in an eighth embodiment, the present invention is directed to a method of assessing in vitro efficacy of a vaccine comprising:

(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 Or 4 after the initial vaccine addition, and on one of day 5, 6 or 7 after the initial vaccine addition;

(b) Ruining a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;

(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and (d) analyzing supernatant and/or cells from the cell culture of (c) for production of an antibody with binding specificity for the vaccine-specific antigen by the B cells, thereby assessing in vitro efficacy of a vaccine.

In a further example, and in a ninth embodiment, the present invention is directed to a method of predicting in vivo efficacy of a vaccine using an in vitro cell culture comprising:

(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody IL-2, 1L-6, IL-21, and 1L-23, and
wherein irradiated feeder cells and additional vaccine are added on one of day 2, 3 or 4 after the initial vaccine addition, and on one of day 5, 6 or 7 after the initial vaccine addition;
(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and
(d) analyzing supernatant and/or cells from the cell culture of (c) for production of an antibody with binding specificity for the vaccine-specific antigen by the B cells, wherein when such antibody is found the vaccine is predicted to have in vivo efficacy.

In aspects of these seventh, eighth and ninth embodiments, the irradiated feeder cells may be, but are not limited to, cord blood mononuclear cells (CBMCs) grown in a serum-free culture media.

In aspects of these seventh, eighth and ninth embodiments, the vaccine maybe, but is not limited to, an inactivated, attenuated, toxoid, subunit, conjugate, valence and heterotypic vaccine, or a protein, peptide, polynucleotide, oligonucleotide, polysaccharide, virus, virion, bacteria, fungi, or fragment thereof, or antigen-primed DCs.

In aspects of these seventh, eighth and ninth embodiments, the vaccine-specific antigen may be, but is not limited to, a portion of the vaccine or a component of the vaccine.

In aspects of these seventh, eighth and ninth embodiments, the cord blood B cells may be treated with CpG2006 prior to addition of the cord blood B cells to the second cell culture.

In aspects of these seventh, eighth and ninth embodiments, the matrix may be a gel matrix.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same proposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

In FIG. 5A, data illustrates IgM antibody magnitude (represented in MSD units) while in FIG. 5B, data shows stimulation index (SI) or fold change over background Hib-TT control. % above each bar represents # of donors where the SI was ≥1.5.

In FIG. 6A, data illustrates IgG antibody magnitude (represented in MSD units) while in FIG. 6B, data shows stimulation index (SI) or fold change over background Hib-TT control. % above each bar represents # of donors where the SI was ≥1.5.

DETAILED DESCRIPTION OF THE INVENTION

I. Definitions

Figure 1:
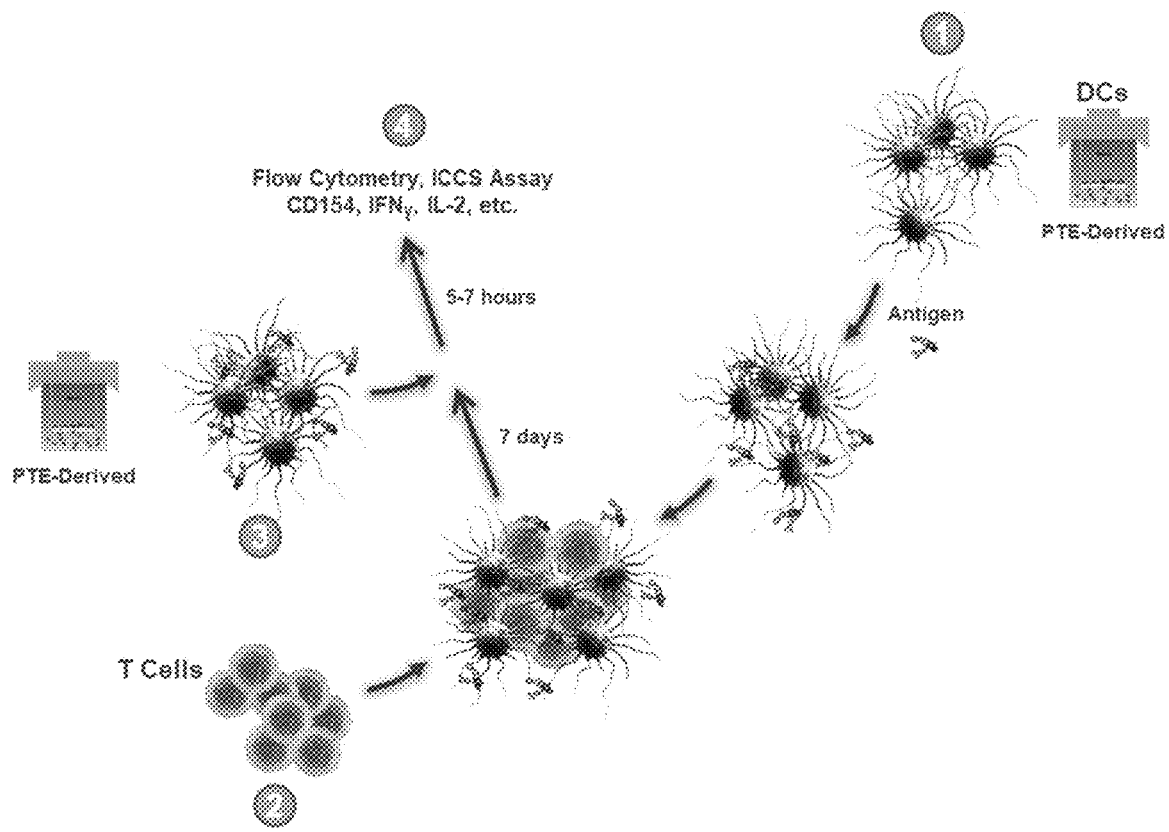
FIG. 1. nMIMIC DCI D4+ T Cell Model for Evaluating a Selected Antigen. Neonate DCs that are pre-treated with a selected antigen for 24 hrs (1) are co-cultured with CD4+ T cells (2) for 7 days. The co-culture is then re-challenged with antigen-treated DCs (3) for 5-7 hours prior to analysis (4). Analysis may include assaying cytokine expression via such means as flow cytometry, intracellular cytokine staining (ICCS).

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, an "antigen" refers to an agent (e.g., protein, polypeptide, polysaccharide, glycolipid, etc.) that elicits an immune response; and/or an agent that is bound by a T cell receptor (e.g., when presented by an MHC molecule), Fc receptor (e.g., activating Fc receptors expressed in high levels by dendritic cells and macrophages), B cell receptor or to an antibody (e.g., produced by a B cell) when exposed or administered to an organism. In some embodiments, an antigen elicits a humoral response (e.g., including production of antigen-specific antibodies) in an organism. Alternatively or additionally, in some embodiments, an antigen elicits a cellular response (e.g., involving T-cells whose receptors specifically interact with the antigen) in an organism.

As used herein, a "vaccine" refers to an administerable, prophylactic compound, composition, or substance that is capable of stimulating an immune response (e.g., containing an antigen), which confers protection against infection (or ameliorates the symptoms of infection) by a causative agent of a disease (e.g., virus, bacterium, fungus, etc.).

As used herein, an "adjuvant" refers to a substance or vehicle that non-specifically enhances the immune response to an antigen. Adjuvants can include a suspension of minerals (alum, aluminum hydroxide, or phosphate) on which antigen is adsorbed; or water-in-oil emulsions in which an antigen solution is emulsified in mineral oil (for example, Freund's incomplete adjuvant), sometimes with the inclusion of killed mycobacteria (Freund's complete adjuvant) to further enhance antigenicity, and oil-in-water emulsions (e.g., MF59, AS03). Immunostimulatory oligonucleotides (such as those including a CpG motif) can also be used as adjuvants. Adjuvants also include biological molecules, such as costimulatory molecules. Exemplary biological adjuvants include IL-2, GM-CSF, TNF-α, IFN-γ, G-CSF, LFA-3, CD72B7-1, B7-2, OX-40L and 41 BBL.

II. The Present Invention

As summarized above, the present invention provides cell culture constructs and methodologies that together serve as in vitro models of the mammalian neonatal immune system. Because the constructs are cell cultures comprising cord blood and cord blood-derived immune cells, the constructs are termed neonatal modular immune in vitro constructs (nMIMIC). These nMIMIC models can be used to predict early life immune responses to selected agents, such as antigens, and they can also serve as primary screens in the pre-clinical evaluation of infant and toddler vaccines.

The nMIMIC models utilize cord blood immune cells. Use of such cells is the only practical approach to studying early life immunity in vitro due to the practicality and ethical issues associated with obtaining large enough volumes of blood from neonates, infants, and toddlers for cell studies. Cord blood mononuclear cells (CBMCs), for example, may be obtained from blood banks across the United States.

While some groups have utilized cord blood to assess immune responses, as seen in the published literature, none offers a system where the balance of cellular components of the mammalian immune system are considered, such as the ratios of types and concentration of cells, multicellular interactions, and spatiotemporal cellular kinetics. With the nMIMIC models presented herein, human neonatal and infant immune response profiles are replicated. Importantly, statistically significant neonatal immune response to vaccination can be achieved in the nMIMIC models with much fewer donor samples (20-40 CBMC samples) than is required for a clinical trial where hundreds (phase 2 trials) or even thousands (phase 3 trials) of infant participants would be necessary. These assays can be performed at a fraction of the cost it would take to run even a small clinical trial. Experimental data produced to date provides strong evidence that the nMIMIC models can serve as in vitro biomimetic systems to assess immunogenicity of various vaccines, such as bacterial conjugate formulations. The nMIMIC model system not only encompasses a very practical and achievable approach, it provides a powerful tool for assessing immunological responses in a human infant immune system without the need to employ the human component, i.e., infants. This provides for decisional outcomes on the formulation and use of new or modified vaccines prior to conducting a complex clinical trial.

As also summarized above, the nMIMIC models of the invention offer the ability to utilize components of the mammalian neonatal immune system (e.g., T, B, and dendritic cells) from cord blood and present them in culture at ratios similar to that observed under physiological conditions in vivo. With these models, the inventors have been able to (1) generate cell-mediated responses using cord blood derived-dendritic cells (DCs) and CD4+ T cells, and (2) generate antigen-specific antibody responses to childhood vaccines using cord blood-derived $T_{FH}$ cells and naïve B cells.

The present invention can thus, be defined based on two nMIMIC models, the nMIMIC DC/T cell model and the nMIMIC B cell/$T_{FH}$ cell model, and methods of using these models to provide information about cellular responses of components of the mammalian neonatal immune system to antigens and in assessing candidate vaccines.

nMIMIC DC/T Cell Model

The nMIMIC DC/T cell model is the first of the two nMIMIC models of the present invention. This model primarily comprises cord-blood derived dendritic cells (DCs) and cord blood CD4+ T cells, and it can be used, for example, to assay the effects of selected agents on neonatal antigen presentation and CD4+ T cell response. Because neonatal immune systems are immature, the responses of such systems to antigens and vaccines can differ from those seen in juvenile and adult immune systems. Therefore, this model can be used to study the intricacies of the neonatal immune system as well as to obtain important information regarding the likely response of an infant to a selected antigen or vaccine.

In the broadest sense, the nMIMIC DC/T cell model is utilized by (i) preparing or obtaining a population of cord blood-derived dendritic cells (DCs), (ii) exposing the DCs to a selected agent and permitting uptake, (iii) culturing these primed DCs with cord blood CD4+ T cells, and (iv) assessing the responses of the cells. Use of this model thus allows one to study such disparate functionalities as agent uptake and presentation by neonatal DCs, interactions between primed DCs and CD4+ T cells, and the cellular response of CD4+ T cells when activated by printed DCs.

While it will be readily apparent that the nMIMIC DC/T cell model can be used in a number of different manners, it can be generally characterized as an in vitro method of assessing the response of cells of the neonatal immune system to a selected agent. Thus, the invention is directed to a method of assessing a cellular response to a selected agent comprising:

(a) adding a selected agent to a first in vitro cell culture comprising cord blood-derived dendritic cells (DCs) and maintaining the cell culture under conditions promoting uptake of the selected agent by the DC's to, form a first population of primed DC's, (b) forming a second in vitro cell culture comprising primed DCs developed in (a) and cord blood CD4+ T cells and maintaining the cell culture wider conditions promoting T cell activation, (c) adding a second population of primed DCs to the cell culture of (b) and maintaining the culture under conditions promoting a T cell response, wherein the second population of primed Des is prepared in the same manner as the first population of primed DCs, and (d) analyzing supernatant and/or T cells from the cell culture of (c) for a T cell response, thereby assessing a cellular response to a selected agent.

The nMIMIC DC/T cell model can also be characterized as an in vitro method of screening selected agents (e.g.,. antigen, vaccine) for their activity on components of the mammalian neonatal immune system. Thus, the invention is also directed to a method of screening a selected agent for activity comprising:

(a) adding a selected agent to a first in vitro cell culture comprising cord blood-derived dendritic cells (DCs) and maintaining the cell culture under conditions promoting the selected agent uptake by the DCs to form a first population of primed DCs, (b) forming a second in vitro cell culture comprising primed DCs developed in (a) and cord blood CD4+ T cells and maintaining the cell culture under conditions promoting T cell activation, (c) adding a second population of primed DCs to the cell culture of (b) and maintaining the culture under conditions promoting a T cell response, wherein the second population of primed DCs is prepared in the same manner as the first population of primed DCs, and (d) analyzing supernatant and/or T cells from the cell culture of (c) for a T cell response, thereby screening a selected agent for activity.

When this model is used, the first cell culture is maintained for a period of time that will vary depending on the culture conditions and identity of the antigen, among other important factors. However, the first cell culture will generally be maintained for between about 1 and 48 hours prior to formation of the second cell culture. Suitable periods of time include about 1, 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more hours prior to formation of the second cell culture, and about 12-36 hours, about 15-33 hours, about 18-30 hours, and about 21-27 hours.

When this model, is used, the second cell culture is maintained for a period of time that will also vary depending on the culture conditions and identity of the antigen, among other important factors. However, the second cell culture will generally be maintained for between about 1 and 20 days prior to adding the second population of primed DCs. Suitable periods of time include about 1, 2, 3, 4, 5, 6, 7, 8, 9, 10, 11, 12, 13, 14, 15, 16, 17, 18, 19, 20 or more days prior to adding the second population of primed DCs, and about 10-20 days, about 12-20 days, about 14-10 days, about 16-20 days, about 12-16 days, about 14-16 days, about 4-10 days, about 5-10 days, and about 6-8 days.

When this model is used, the culture of (c) is maintained for a period of time that will again vary depending on the culture conditions and identity of the antigen, among other important factors. However, the culture of (c) will generally be maintained for between about 1 and 10 hours prior to the analyzing of (d). Suitable periods of time include about 1, 2, 3, 4, 5, 6, 7, 8, 9, 10, 11, 12 or more hours prior to the analyzing of (d), and about 6-12 hours, about 8-12 hours, about 10-12 hours, about 8-10 hours, about 2-8 hours, about 3-7 hours, and about 4-6 hours.

When this model is used, the T cell response that is analyzed may be production of a cytokine or a marker, for example. Exemplary cytokines include, but are not limited to, one or more of TNFα, IFNγ, IL-2, IL-4, IL-5, IL-6, IL-8, IL-9, IL-10, IL-13, IL-17A, IL-17F, IL-18, IL-21, IL-22, and IL-26. Exemplary markers include, but are not limited to, one or more of CD25, CD26, CD27, CD28, CD30, CD44, CD69, CD71, CD134, and CD154.

The skilled artisan will understand that the selected agent that may be used in this model or any of the other models of the invention can vary widely and it is only limited by the ability to be taken up and displayed by the DCs. Suitable agents can be generally defined as antigens and vaccines, and they can be further defined as proteins, peptides, polynucleotides, oligonucleotides, and polysaccharides, as well as viruses, virions, bacteria, fungi, and fragments thereof.

The immune cells that can be, used in the nMIMIC DC/T cell model can be from a single cord blood source or two or more sources, depending on the manner in which the model is being used. Thus, for example, the cord blood T cells can be autologous to the cord blood-derived DCs (i.e., from the same organism), or allogeneic to the cord blood-derived DCs (i.e., from another organism of the same species).

The ratio of primed DCs to cord blood T cells in the culture of (b) can vary depending on such factors as the manner in which the model is used, the identity of the selected agent, and the other components included in the culture. The ratio of DCs to T cells may range from about 1:5 to about 1:100. For most applications, the ratio may range from about 1:20 to about 1:80 or about 1:30 to about 1:50, although acceptable ranges also include from about 1:10 to about 1:50, about 1:20 to about 1:60, about 1:15 to about 1:35, and about 1:30 to about 1:55.

In a similar fashion, the ratio of cells in the second population of primed DCs added to the culture of (c) to the cord blood T cells in the culture can vary depending on such factors as the manner in which the model is used, the identity of the selected agent, and the other components included in the culture. The ratio of DCs to T cells may range from about 1:5 to about 1:100. For most applications, the ratio may range from about 1:5 to about 1:50 or from about 1:5 to about 1:15, although acceptable ranges also include from about 1:5 to about 1:20, about 1:10 to about 1:25, about 1:15 to about 1:30 and about 1:20 to about 1:40.

In aspects of these embodiments, the cord blood-derived DCs may be characterized as expressing one or more of the following markers: CD14, CD16, CD25, CD80, CD86, and HLA-DR.

The cord blood-derived DCs that are used in the nMIMIC DC/T cell model can be prepared in conjunction with the use of the model or obtained from another, commercial source. The DCs can be obtained from an active cell culture, or prepared from a frozen aliquot of the cells. In one aspect of the invention, the cord blood-derived DCs may be prepared by a method comprising:

(a) culturing endothelial cells on an upper surface of a porous membrane, wherein said porous membrane is housed in an upper chamber of a cell culture well that is suspended over, and is separable from, a lower chamber of the well;
(b) applying cord blood mononuclear cells (CBMCs) to the endothelial cells on the porous membrane of (a);
(c) removing the upper chamber housing the porous membrane and endothelial cells from the well about 4.8 hours after application of the CBMCs; and
(d) isolating dendritic cells from the lower chamber of the well.

In the noted method of preparing the cord blood-derived DCs, the porous membrane may be a polycarbonate membrane or a membrane comprised of polytetralluoroethylene, polyethylene terephthalate, or polyester (PET). The porous membrane typically have pores that allow cells, e.g., monocytes and immature dendritic cells, to pass through. Such pores range in diameters of between about 1 and 15 μm, however the pores will generally be between 0.4, 0.5, 0.6, 0.7, 0.8, 0.9, 1, 2, 3, 4, 5, 6, 7, 8,19 10, 11, 12, 13, 14 and 15 μm in diameter. A permeable support may be used to provide the upper chamber of the well, the porous membrane, and the lower chamber of the well. An example of such a permeable support is the Corning Inc. Transwell® permeable supports.

In the methods of preparing the cord blood-derived DCs, the lower chamber of the well may comprise extracellular matrix (ECM) material. The ECM material may comprise a material selected from, but not limited to, gelatin, collagen, synthetic ECM materials, poly(lactic-co-glycolic acid) (PLGA), polyglycolic acid (PGA), natural ECM materials, chitosan, protosan, fibronectin, vitronectin, collagen I, collagen IV, laminin, and mixtures thereof. The lower chamber of the well may further comprise one or more of fibroblasts, support cells, and stromal cells.

In the noted method of preparing the cord blood-derived DCs, the endothelial cells may be, but are not limited to, human umbilical vein endothelial cells (HUVECs) and human somatic cell hybrid EA.hy926 (ATCC® CRL-2922™; ATCC, Manassas, Va.). In additional aspects, the endothelial cells may be a transformed endothelial cell line.

In the noted method of preparing the cord blood-derived DCs, the endothelial cells may he cultured on the both sides of the porous membrane. Further, the endothelial cells may be cultured to confluency prior to adding the CBMCs. Alternatively, the endothelial cells may be cultured until multilayer cell growth is achieved and prior to adding the CBMCs.

In the noted method of preparing the cord blood-derived DCs, a layer of ECM material may be on the upper surface of the porous membrane and the endothelial cells are cultured on the ECM material layer. Alternatively, a layer of ECM material may be on the upper surface and the lower surface of the porous membrane and the endothelial cells are cultured on both layers of ECM material, The ECM material may comprise a material selected from, but not limited to, gelatin, collagen, synthetic ECM materials, PLGA, PGA, natural ECM materials, chitosan, protosan, fibronectin, vitronectin, collagen I, collagen IV, laminin, and mixtures thereof.

When the nMIMIC DC/T cell model is used in conjunction with the noted method of preparing the cord blood-derived DCs, the lower chamber of the well that is used to prepared the dendritic cells may also serve as the first cell culture of (a). Alternatively, the first cell culture of (a) can be is a separate culture to which the DCs are transferred.

nMIMIC B Cell/$T_{FH}$ Cell Model

The nMIMIC B cell/$T_{FH}$ cell model is the second of the two nMIMIC models of the present invention. This model comprises cord-blood derived T follicular helper ($T_{FH}$) cells and cord blood B cells, and it can be used, for example, to assay the effects of selected agents on neonatal antigen presentation and B cell response. As with the nMIMIC DC/T cell model, this model can also be used to study the intricacies of the neonatal immune system as well as to obtain important information regarding the likely response of an infant to a selected antigen or vaccine.

In the broadest sense, the nMIMIC B cell/$T_{FH}$ cell, model is utilized by (i) preparing a population of cord blood-derived T follicular helper ($T_{FH}$) cells from cord, blood CD4+ T cells in the presence of a selected agent, (ii) preparing a second cell culture comprising these $T_{FH}$ cells and naïve cord blood B cells, (iii) adding additional agent or a fragment thereof to the culture, and (iv) assessing the responses of the cells. Use of this model thus allows one to study such disparate functionalities as $T_{FH}$ cell maturation, agent uptake and presentation by $T_{FH}$ cells, interactions between primed $T_{FH}$ cells and B cells, and the cellular response of $T_{FH}$ cells and B cells.

While it will be readily apparent that the nMIMIC B cell/$T_{FH}$ cell model can be used in a number of different manners, it can be generally characterized as an in vitro method of assessing the response of cells of the neonatal immune system to a selected vaccine. Thus, the invention is directed to a method of screening a vaccine for activity comprising:
(a) adding a vaccine and one or more cellular activator to a first in vitro cell culture comprising cord blood CD4+ T cells and maintaining the cell culture under conditions promoting development of vaccine-specific T follicular helper ($T_{FH}$) cells,
(b) forming a second in vitro cell culture comprising $T_{FH}$ cells developed in (a) and cord blood B cells,
(c) adding a vaccine-specific antigen to the cell culture of (b) and maintaining the culture under conditions promoting a cellular response, and
(d) analyzing supernatant and/or cells from the cell culture of (c) for a cellular response, thereby screening a vaccine for activity.

The nMIMIC B cell/$T_{FH}$ cell model can also be characterized as an in vitro method of assessing the potential efficacy of a vaccine via in vitro testing. Thus, the invention is also directed to a method of assessing efficacy of a vaccine comprising:
(a) adding a vaccine and one or more cellular activator to a first in vitro cell culture comprising cord blood CD4+ T cells and maintaining the cell culture under conditions promoting development of vaccine-specific T follicular helper ($T_{FH}$) cells,
(b) forming a second in vitro cell culture comprising $T_{FH}$ cells developed in (a) and cord blood B cells,
(c) adding a vaccine-specific, antigen to the cell culture of (b) and maintaining the culture under conditions promoting a cellular response, and
(d) analyzing supernatant and/or cells from the cell culture of (c) for a cellular response, thereby assessing efficacy of a vaccine.

The nMIMIC B cell/$T_{FH}$ cell model can further be characterized as an in vitro method of predicting in vivo efficacy of a vaccine using an in vitro cell culture. Thus, the invention is also directed to a method of predicting in vivo efficacy of a vaccine using an in vitro cell culture comprising:
(a) adding a vaccine and one or more cellular activator to a first cell culture comprising cord blood CD4+ T cells and maintaining the cell culture under conditions promoting development of vaccine-specific T follicular helper ($T_{FH}$) cells,
(b) forming a second cell culture comprising $T_{FH}$ cells developed in (a) and cord blood B cells,
(c) adding a vaccine-specific antigen to the cell culture of (b) and maintaining the culture under conditions promoting a cellular response, and
(d) analyzing supernatant and/or cells from the cell culture of (c) for a cellular response, wherein when a cellular response is found the vaccine is predicted to have in vivo efficacy.

In addition, the nMIMIC B cell/$T_{FH}$ cell model can be characterized as an in vitro method of assessing the immunogenicity of an antigen. Thus, the invention is also directed to a method of assessing immunogenicity of an antigen comprising:
(a) adding an antigen and one or more cellular activator to a first in vitro cell culture comprising cord blood CD4+ T cells and maintaining the cell culture under conditions promoting development of antigen-specific T follicular helper ($T_{FH}$) cells,
(b) forming a second in vitro cell culture comprising $T_{FH}$ cells developed in (a) and cord blood B cells,
(c) adding the antigen to the cell culture of (b) and maintaining the culture under conditions promoting a cellular response, and
(d) analyzing supernatant and/or cells from the cell culture of (c) for a cellular response, thereby assessing immunogenicity of an antigen.

When this model is used, the first cell culture is maintained for a period of time that will vary depending on the culture conditions and identity of the vaccine/antigen, among other important factors. However, the first cell culture will generally be maintained for between about 1 and 20 days. Suitable periods of time include about 1, 2, 3, 4, 5, 6, 7, 8, 9, 10, 11, 12, 13, 14, 15, 16, 17, 18, 19, 20 or more days, and about 7-13 days, about 8-12 days, and about 9-11 days.

When this model is used, additional vaccine/antigen may be added to the first cell culture including at least once, twice, thrice, or more. The additional vaccine/antigen may be identical to the initial vaccine/antigen added to the first cell culture. Alternatively, the additional vaccine/antigen may be a different vaccine/antigen that stimulates an immune response against the same pathogen or disease to which the initial vaccine/antigen is directed or derived. For example, the initial vaccine/antigen may comprise one or more antigens from a particular virus or bacteria, and the additional vaccine/antigen may comprise one or more different antigens from the same virus or bacteria. The additional vaccine/antigen may also be a different formulation of the initial vaccine/antigen. For example, the initial vaccine/antigen may be adjuvanted, and the additional vaccine/antigen may be unadjuvanted. In a particular aspect, the additional vaccine/antigen is added to the first cell culture at least once. Irradiated feeder cells may be added to the first culture upon one or more of the repetitions of vaccine/antigen addition. The irradiated feeder cells may be, but are not limited to, cord blood mononuclear cells (CBMCs).

When additional vaccine/antigen is added, it may be added on day 2, 3 or 4 after the initial vaccine/antigen addition, and/or additional vaccine/antigen is added on day 5, 6 or 7 after the initial vaccine/antigen addition. In a particular aspect, the first cell culture is maintained for a period of about 8-12 days and additional vaccine/antigen is added on one of day 2, 3, or 4 and added on one of day 5, 6 or 7 after the initial vaccine/antigen addition.

When this model is used, the antigen or vaccine-specific antigen added in (c) is added shortly after the cell culture of (b) is prepared, i.e., within about 1, 2, 3, 4, 5, 6 or more hours after preparation of the cell culture of (b). The identity of the vaccine-specific antigen used in this model will vary widely based on the identity of the vaccine, but such antigens are typically a portion of the vaccine or a component of the vaccine. The antigen or vaccine-specific antigen added in (c) may be identical to the initial vaccine antigen added in (a). Alternatively, the antigen or vaccine-specific antigen added in (c) may be different from (i.e., not present in) the vaccine/antigen added in (a). Alternatively, the antigen or vaccine-specific antigen added in (c) may be different from the vaccine/antigen added in (a), but may be capable of stimulating an immune response against the same pathogen or disease to which the vaccine/antigen of step (a) is directed. For example, the vaccine/antigen added in step (a) may comprise one or more antigens from a particular virus or bacteria (e.g. a polysaccharide), and the additional vaccine/antigen may comprise one or more different antigens from the same virus or bacteria (e.g., a polypeptide).

When this model is used, the culture of (c) is also maintained for a period of time that will vary depending on the culture conditions and identity of the vaccine or antigen, among other important factors. However, the culture of (c) will generally be maintained for between about 1 and 25 days. Suitable periods of time include about 1, 2, 3, 4, 5, 6, 7, 8, 9, 10, 11, 12, 13, 14, 15, 16, 17, 18, 19, 20, 21, 22, 23, 24, 25 or more days, and about 10-20 days, about 12-18 days, about 14-16 days, about 7-13 days, about 8-12 days, and about 9-11 days.

In aspects of these embodiments, IL-21 may be added to the culture of (c). The amount added may vary, but the final concentration in the culture media will generally range from about 1 to 500 ng/ml. Suitable concentration ranges include from about 10 to 500 ng/ml, 1 to 100 ng/ml, 50 to 350 ng/ml, 50 to 150 ng/ml, 100 to 400 ng/ml, 150 to 500 ng/ml, and 200 to 50 ng/ml.

When IL-21 is added, IL-21 may be added at one or more of the following time points: (i) when the antigen or vaccine-specific antigen is added to the second cell culture of (b) (ii) on day 2, 3 or 4 after preparation of the second cell culture, and (iii) on day 5, 6 or 7 after preparation of the second cell culture. In a particular aspect, the culture of (c) is maintained for about 8-12 10 days and IL-21 is added upon addition of the antigen or vaccine-specific antigen to the second cell culture, on one of three days 2, 3 or 4 after preparation of the second cell culture, and on one of six days 5, 6 or 7 after preparation of the second cell culture.

When this model is used, the cellular response is one or more of production of a cytokine by the $T_{FH}$ cells, expression of a marker by the T cells, production of a cytokine by the B cells, expression of a marker by the B cells, and production of an antibody with binding specificity for the antigen or vaccine-specific, antigen by the B cells. The cytokine may be, but is not limited to, is one or more of CXCL13, TNFα, IFNγ, IL-2, IL-4, IL-6, IL-8, IL-10, IL-13, IL-17, and IL-21. The marker may be, but is not limited to, is one or more of CD10, CD19, CD20, CD24, CD27, CD38, CD40CD86, CD138, IgD, IgG, and IgM.

The skilled artisan will understand that the vaccine or antigen that may be used in this model can vary widely and it only limited by the ability to be processed by $T_{FH}$ cells and presented to B cells. Suitable vaccines can be generally defined as inactivated, attenuated, toxoid, subunit, conjugate, valence and heterotypic vaccines, and they can be further defined as proteins, peptides, polynucleotides, oligonucleotides, and polysaccharides, as well as microorganisms such as viruses, virions, bacteria, and fungi, and fragments thereof, and antigen primed DCs.

The one or more cellular activator used in this model may be, but is not limited to, an anti-CD28 antibody, IL-2, IL-6, IL-12, IL-21, and IL-23.

The immune cells that can be used in the nMIMIC B cell/$T_{FH}$ cell model can be from a single cord blood source or two or more sources, depending on the manner in which the model is being used. Thus, for example, the cord blood B cells can be autologous to the cord blood CD4+ T from which the $T_{FH}$ cells are derived (i.e., from the same organism). The cord blood B cells can even be heterologous to the cord blood CD4+ T cells (i.e., from an organism of a different species).

When this model is used, the cord blood B cells may be treated with CpG2006 (ODN 2006; InvivoGen, San Diego, Calif.) prior to addition of the cord blood B cells to the second cell culture of (b). When CpG2006 is used, the B cells are treated with the activator for about 1-48 hours before forming the second cell culture of (b) at a concentration of between about 0.1 to 5 ug/ml.

The ratio of $T_{FH}$ cells to cord blood B cells in the second cell culture can vary depending on such factors as the manner in which the model is used, the identity of the selected agent (vaccine or antigen), and the other components included in the culture. For most applications, the ratio may range from about 1:1 to about 1:100.

When this model is used, the second cell culture may be formed in a three-dimensional matrix. The matrix may be, but is not limited to, a gel matrix, such as a hydrogel for 3D cell culture. The matrix may contain one or more extracellular matrix components, including, but not limited to, one or more of collagen I, collagen IV, vitronectin, fibronectin, and laminin.

In a particular example, the invention is directed to a method of screening a vaccine for activity in vitro comprising:
(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12 L-21, and IL-23, and
wherein irradiated feeder cells and additional vaccine are added on one of day 2, 3 or 4 after the initial vaccine addition, and on one of day 5, 6 or 7 after the initial vaccine addition;
(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and (d) analyzing supernatant and/or cells from the cell culture of (c) for production of an antibody with binding specificity for the vaccine-specific antigen by the B cells, thereby screening a vaccine for activity in vitro.

In another example, the invention is directed to a method of assessing in vitro efficacy of a vaccine comprising:
(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 or 4 after the initial vaccine addition, and on one of day 5, 6 or 7 after the initial vaccine addition;
(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and
(d) analyzing supernatant and/or cells from the cell culture of (c) for production of an antibody with binding specificity for the vaccine-specific antigen by the B cells, thereby assessing in vitro efficacy of a vaccine, In a further example, the invention is directed to a method of predicting in vivo efficacy of a vaccine using an in vitro cell culture comprising:
(a) adding a vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine, are added on one of day 2, 3 or 4 after the initial vaccine addition, and on one of day 5, 6 or 7 after the initial vaccine addition;
(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and
(d) analyzing supernatant and/or cells from the cell culture of (c) for production of an antibody with binding specificity for the vaccine-specific antigen by the B cells, wherein when such antibody is found the vaccine is predicted to have in vivo efficacy.

In these examples, the irradiated feeder cells may be, but are not limited to, cord blood mononuclear cells (CBMCs).

The skilled artisan will understand that the vaccine that may be used in this model can vary widely and it only limited by the ability to he processed by $T_{FH}$ cells and presented to B cells. Suitable vaccines can be generally defined as inactivated, attenuated, toxoid, subunit, conjugate, valence and heterotypic vaccines, and they can be further defined as proteins, peptides, polynucleotides, oligonucleotides, and polysaccharides, as well as microorganisms such as viruses, virions, bacteria, and fungi, and fragments thereof, and antigen-primed DCs.

The vaccine-specific antigen used in this model will vary widely based on the identity of the vaccine, but such antigens are typically a portion of the vaccine or a component of the vaccine.

The cord blood B cells may be treated with CpG2006 prior to addition of the cord blood B cells to the second cell culture. When CpG2006 is used, the B cells are treated with the activator for about 1-48 hours before forming the second cell culture of (b) at a concentration of between about 0.1 to 5 ug/ml.

The matrix may be, but is not limited to, a gel matrix, such as a hydrogel for 3D cell culture.

General Features Applicable to Both Models

In each of the embodiments and aspects of the invention, the analysis of supernatants and cell culture media for the production and/or presence of cytokines, markers and other factors may be conducted by via means readily known to and understood by the skilled artisan that include, but are not limited to, a cytokine/chemokine magnetic bead panel (e.g., Millipore's MILLIPLEX MAP™ kit), an ELISA or MSD (mesoscale scale discovery) multi-array technology.

In each of the embodiments and aspects of the invention, the analysis of cells, such as $T_{FH}$ cells, T cells and B cells, for production and/or expression of cytokines, cell surface markers and other factors may be conducted via means readily known to and understood by the skilled artisan that include, but are not limited to, flow cytometry using one or more antibodies that bind to selected molecules with specificity.

In each of the embodiments and aspects of the invention, the analysis of supernatants and cell culture media for the production of antibodies may be conducted via means readily known to and understood by the skilled artisan that include, but are not limited to, a magnetic bead panel, an ELISA of MSD multi-array technology. Similarly, the analysis of B cells for the production of antibodies may be conducted via means readily known to and understood by the skilled artisan that include, but are not limited to, a magnetic bead panel, an ELISA or MSD multi-array technology.

In each of the embodiments and aspects of the invention, culture conditions promoting a cellular response, such as a $T_{FH}$ cell, T cell, and/or B cell response, include culture conditions typically associated with the culture of immune cells in vitro, such as 5% $CO_2$, 95% relative humidity, and 37° C.

In each of the embodiments and aspects of the invention, conditions promoting development of vaccine-specific T follicular helper ($T_{FH}$) cells include culture conditions typical associated with the culture of immune cells in vitro, such as 5% $CO_2$, 95% relative humidity, and 37° C.

In each of the embodiments and aspects of the invention, the source of the cord blood cells may be a human, a non-human primate, bird, horse, cow, goat, sheep, a companion animal, such as a dog, cat or rodent, or other mammal.

III. Examples nMIMIC DC/T Cell Model

Use of the nMIMIC DC cell/T cell model is detailed below and shown schematically in FIG. 1.

Using a peripheral tissue equivalent (PTE) method, human cord blood DCs were generated in a transwell system containing an endothelial cell layer (human somatic cell hybrid EA.hy926 cells). On day 0, EA.hy926 cells were plated in 24-well transwell inserts that had a pore range diameter between about 1 and 15 µm at a density of between $1\times10^4$ and $1\times10^5$ cells in M199 media with 20% FCS (fetal calf serum). On day 6, M199 media was replaced with a serum-free culture media. On day 7, cord blood monocytes (CBMCs) were collected and between $1\times10^6$ and $50\times10^6$ cells in a serum-free culture media were plated onto the 24-well transwell inserts containing the EA.hy926 layer. As DCs migrate through this layer they differentiated into mature cells with the ability to present antigen.

Also, on day 7, a second set of EA.hy926 plated 24-well transwell plates were prepared in M199 media with 20% FCS and cultured for 7 days with media exchange to a serum-free culture media on day 13.

On day 8, transwell inserts of cultures where CBMCs were applied were removed and replaced with a fresh transwell layered with EA.hy926 cells prepared on day 0. At this point DCs had migrated to the bottom of the 24-well dish through the transwell and other cell types still present in transwell insert are removed. Experimental cultures were then treated with antigen of interest at predetermined concentrations to the lower chamber, while control cultures received vehicle alone. In this experiment, the selected antigen was a Haemophilus b tetanus toxoid conjugate vaccine (Hib-TT (Sanofi Pasteur).

On day 9, DCs treated in the presence and absence of antigen were harvested and co-cultured with isolated cord blood CD4+ T cells at ratios between 1:5 and 1:100 (DC:T cells) and incubated for 7 days. Cord blood CD4+ T cells were isolate using negative selection by magnetic bead isolation. On day 14. CBMCs are added to the second set of EA.hy926 transwell plates (prepared on day 7) overnight, with antigen treatments added on day 15 after exchange with fresh EA.hy926 transwells as described above.

On day 16, the first DC/CD4+ T cell co-culture was collected and a second co-culture was prepared with the second set of treated and non-treated transwell-generated DC cells. The first DC/CD4+ T cell co-culture is plated at between $5\times10^4$ and $1\times10^6$ with the second set of harvested DCs plated at between $5\times10^3$ and $1\times10^5$. Re-stimulation with the second set of transwell-generated Des was done for a period of between 2-10 hours prior to intracellular cytokine analysis by flow cytometry.

Intracellular cytokine staining was performed to analyze accumulation of both Th1 (IFNγ, TNFα, IL-2) and Th2 (IL-4, IL-6, IL-10, IL-13) cytokine subsets in response to antigen by flow cytometry using the BD Fortessa® Cytometer with blue, red, and violet lasers using the BD FACS-Diva® Software using the following panel for CD4+ T cell analysis:

|    | Fluorochrome    | Marker  |
|----|-----------------|---------|
| 1  | LDA             | LDA     |
| 2  | BV421           | OX40    |
| 3  | BV605           | TNFα    |
| 5  | BV650           | IL-10   |
| 4  | BV711           | IL-13   |
| 6  | BV785           | IL-4    |
| 7  | FITC            | IL-6    |
| 8  | PE              | CD4     |
| 9  | PE-CF594        | IL-2    |
| 10 | PerCP-eFluor710 | IL-8    |
| 11 | PE-Cy7          | IFNγ    |
| 12 | Alexa Fluor 647 | IL-21   |
| 13 | Alexa Fluor 700 | IL-17A  |
| 14 | APC-Cy7         | CD154   |

Figure 2:
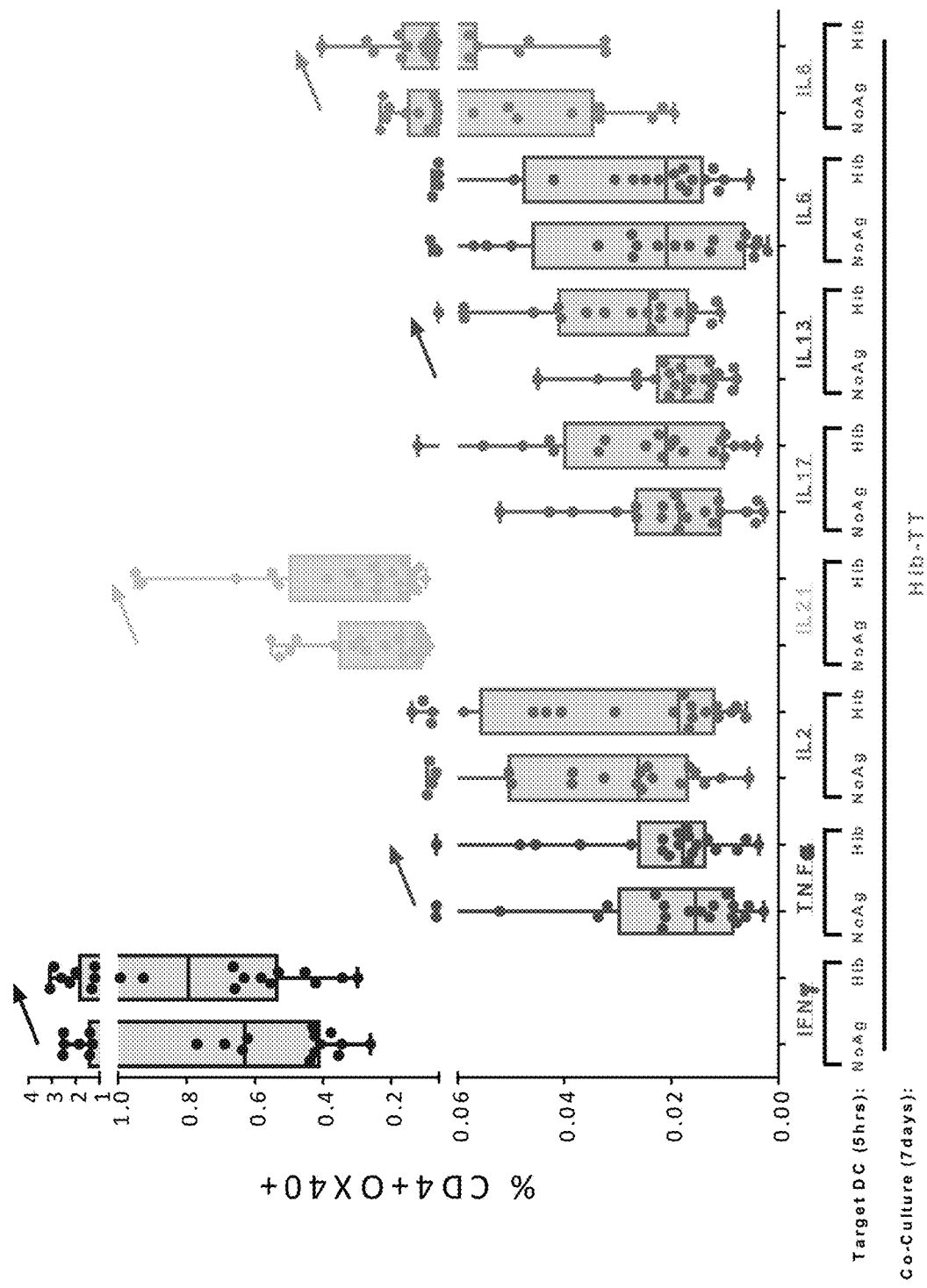
FIG. 2. nMIMIC DC/CD4+ T Cell Model: Stimulation of nMIMIC with Hib-TT ("Hib") leads to activation of antigen-specific. CD4+ T Cells in neonates via flow cytometry Multiple intracellular cytokines were increased in response to Hib-TT in the nMIMIC T cell assay. Cord blood T cells that received antigen-treated DCs were co-cultured for 7 days and either re-stimulated or not with target DCs prior to intracellular cytokine analysis. Second bar in each pair represents those cultures stimulated and re-stimulated with Hib-TT. Data for each cytokine is shown as % CD4+OX40+ cytokine+cells. The data in the graph is represented as a box and whisker plot where the first and third quartiles are at the ends of the box, the median is the line in the interior of the box, and the maximum and minimum of the data set are indicated by the whiskers.

The analysis indicated that. stimulation of the nMIMIC DC/T cell model with Hib-TT leads to activation of antigen-specific CD4+ T cells in neonates. As shown in FIG. 2, multiple intracellular cytokines were increased in response to Hib-TT in the nMIMIC T cell assay as assayed via flow cytometry. Cord blood T cells that received antigen-treated DCs were co-cultured for 7 days and either re-stimulated or not with target DCs prior to intracellular cytokine analysis. Second bar in each colored pair represents those cultured stimulated and re-stimulated with Hib-TT.

Figure 3:
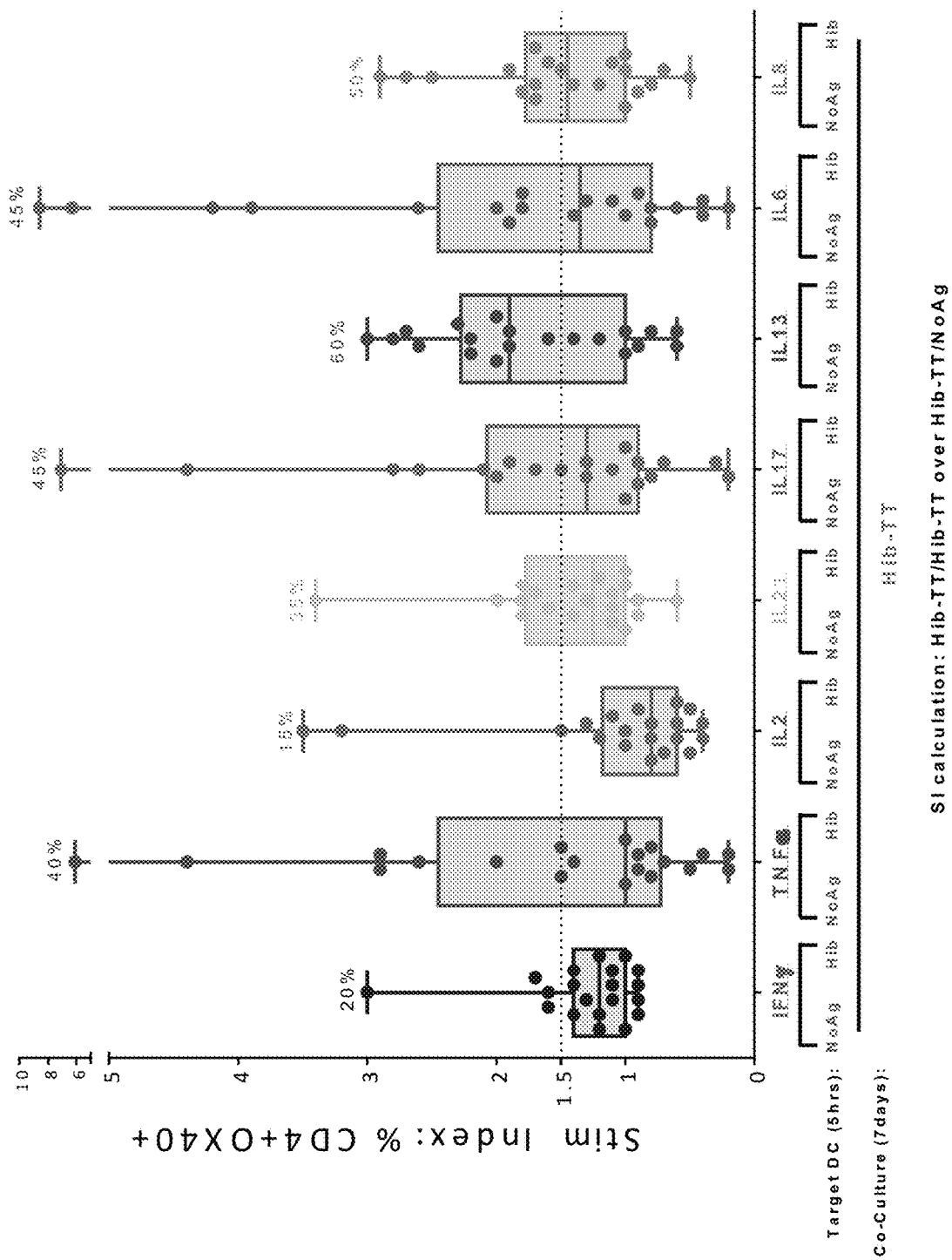
FIG. 3. nMIMIC DC/CD4+ T Cell Model: Stimulation of nMIMIC with Hib-TT ("Hib") leads to activation of CD4+ T cells in neonates via flow cytometry. % above each bar represents # of donors Where the stimulation index (SI) or fold change over background was ≥1.5. Stimulation index was calculated as those cultures treated and re-stimulated with Hib-TT (Hib-TT/Hib-T) over cultures treated but not re-stimulated with Hib-TT (Hib-TT/NoAg). Multiple intracellular cytokines are increased in response to Hib-TT in the nMIMIC T cell assay as demonstrated by SI.

As shown in FIG. 3, production of IFNγ, TNFα, IL-2. IL-21, IL-17, IL-13, IL-6 and IL-8 was also increased, as assayed via flow cytometry. In FIG. 3, % represents the number of donors where the stimulation index (SI) or fold change over background was ≥1.5. Multiple intracellular cytokines were found to be increased in response to Hib-TT in the model, as demonstrated by SI. These results indicate that in response to stimulation with Hib-TT cord blood CD4+ T cells were activated showing Th1 (TNFα, and IL-8), Th2 (IL-13, IL-6), as well as Th17 (IL-17) responses as demonstrated by cytokine evaluations via flow cytometry.

nMIMIC B cell/$T_{FH}$ Cell Model

Figure 4:
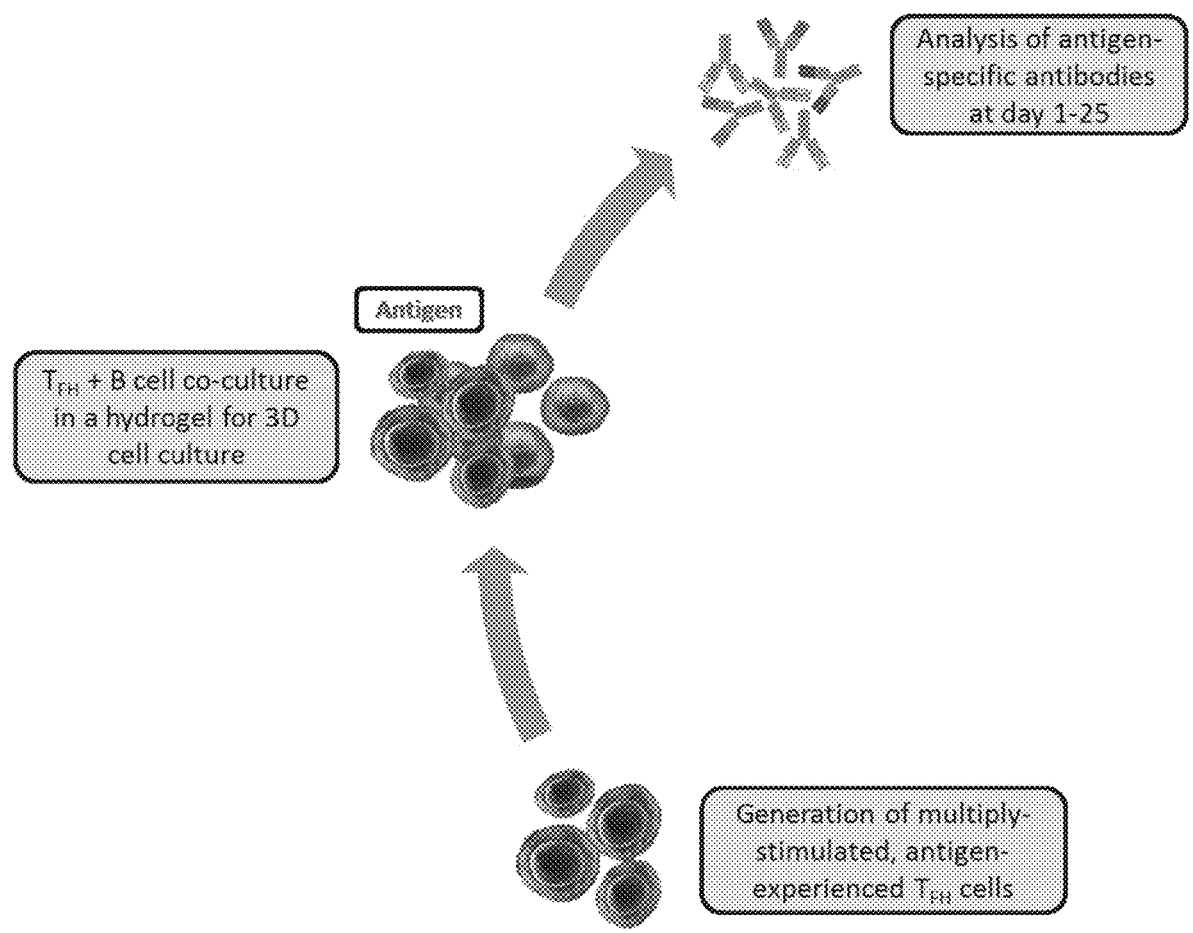
FIG. 4. nMIMIC naïve $T_{FH}$/B cell Model for Evaluating a Selected Antigen. A selected antigen is used to generate antigen-specific cord blood $T_{FH}$ cells. The $T_{FH}$ cells are then co-cultured with B cells, and the combined culture is optionally re-stimulated with antigen before supernatant collection and antibody analyses.

Use of the nMIMIC B cell/$T_{FH}$ cell model is detailed below and shown schematically in FIG. 4.

On day 0 where human cord blood monocytes (CBMCs) were collected and between $1\times10^6$ and $50\times10^6$ cells in a serum-flee culture media were plated in wells of a 24-well culture plate. A first group of wells was treated with a $T_{FH}$ differentiation cocktail containing: a selected antigen (concentration optimized for the selected antigen), anti-CD28 antibodies (0.1 ug/ml to 10 ug/ml), IL-6 (1 ng/ml to 500 ng/ml), and IL-12 (1 ng/ml to 500 ng/ml); a second group of wells was left untreated to serve as feeder cells in later steps; a third group of cells was left untreated to serve as a negative control. The selected vaccines were a meningococcal polysaccharide groups A, C, Y and W-135 diphtheria conjugate vaccine (MenACYW-DT) (Sanofi Pasteur) and Hib-TT(control).

On day 3, CBMCs were harvested from selected wells by vigorous pipetting and/or scraping cells into conical tubes, followed by a rinse with a serum-free culture media. CD4+ T cells were isolated from the harvested CBMC using negative selection by magnetic bead isolation. The CD4+ T cells were then plated in a serum-free culture media at a concentration of $1\times10^5$ and $10\times10^6$ cells per well in 96-well culture plates. Between $1\times10^4$ and $5\times10^5$ irradiated CBMC feeder cells and additional T differentiation cocktail was added to selected wells.

On day 6, additional irradiated feeder cells ($1\times10^3$ to $1\times10^5$) and additional $T_{FH}$ differentiation cocktail was added to selected wells.

On day 10, $T_{FH}$ were harvested from the wells and between $1\times10^4$ and $5\times10^5$ cells were co-cultured with $1\times10^5$ to $10\times10^6$ isolated cord blood B cells (negative magnetic bead selection) in a hydrogel for 3D cell culture. A range of between 1:1 and 1:100 $T_{FH}$ cell to B cell co-culture ratio was prepared. The same antigen that was present in the $T_{FH}$ differentiation cocktail was added to the $T_{FH}$ cell/B cells co-culture.

On day 12, IL-21 was added (1 ng/ml to 500 ng/ml) to the $T_{FH}$ cell/B cell co-culture. On day 14, IL-21 was again added to the $T_{FH}$ cell/B cell co-culture.

On day 20, B cells were harvest from the culture and culture media was collected. IgM and IgG antigen-specific antibody production was analyzed using Meso Scale Discovery 96-well plates coated with all four meningococcal serotype antigens (A, C, Y, W-135). MSDs IgM and IgG secondary antibodies were used to detect antibodies in supernatants.

Figure 5A:
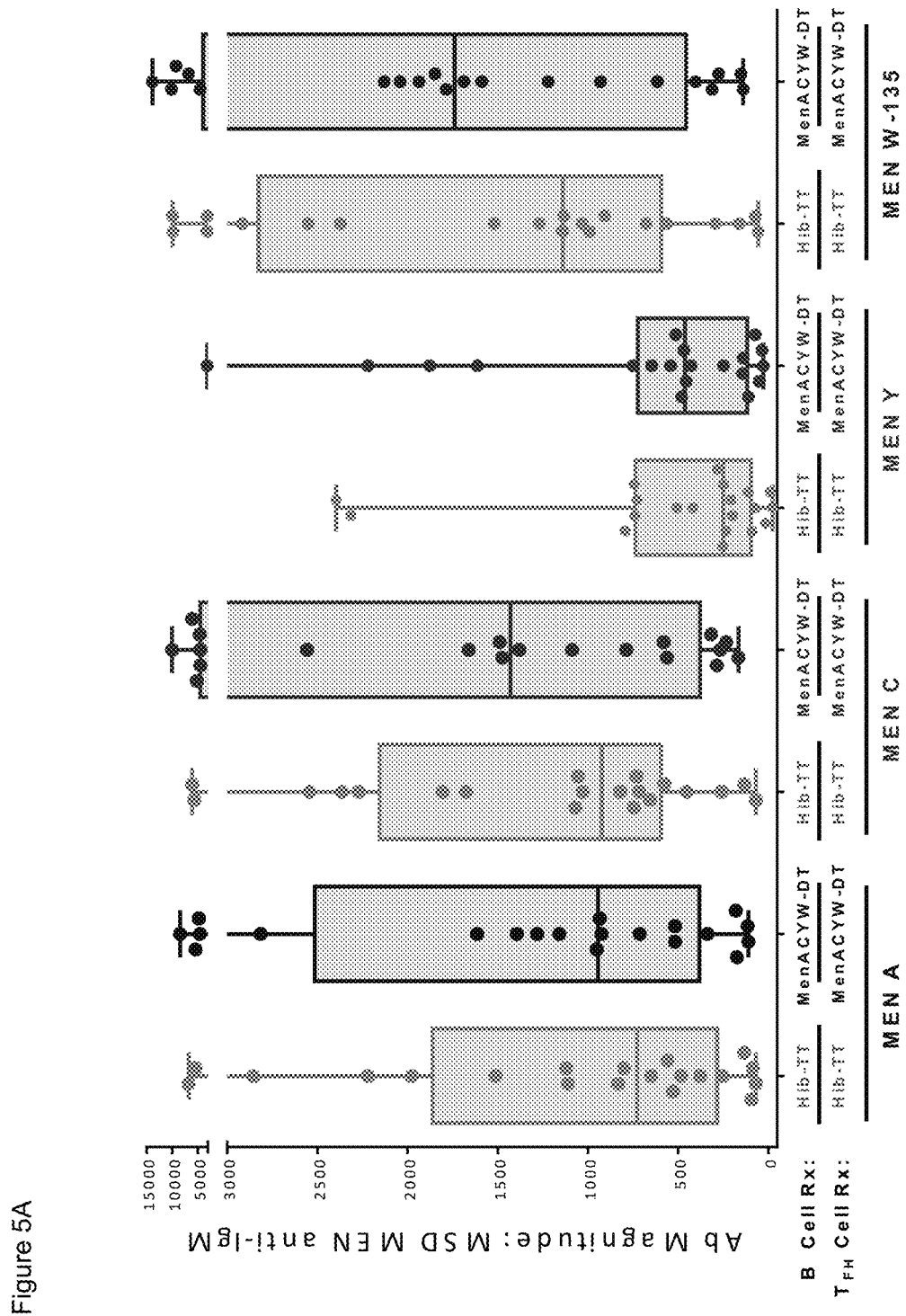
FIGS. 5A-5B. MenACYW-DT-induced IgM antibody responses were observed in the nMIMIC model. MenA-CYW-DT-induced antigen-specific IgM antibody responses in the nMIMIC to all four meningococcal serotypes (A, C, Y, W-135), with several donors showing increased fold changes over background. In these experiments Hib-TT ("Hib") serves as an irrelevant non-meningococcal background control.
Figure 5B:
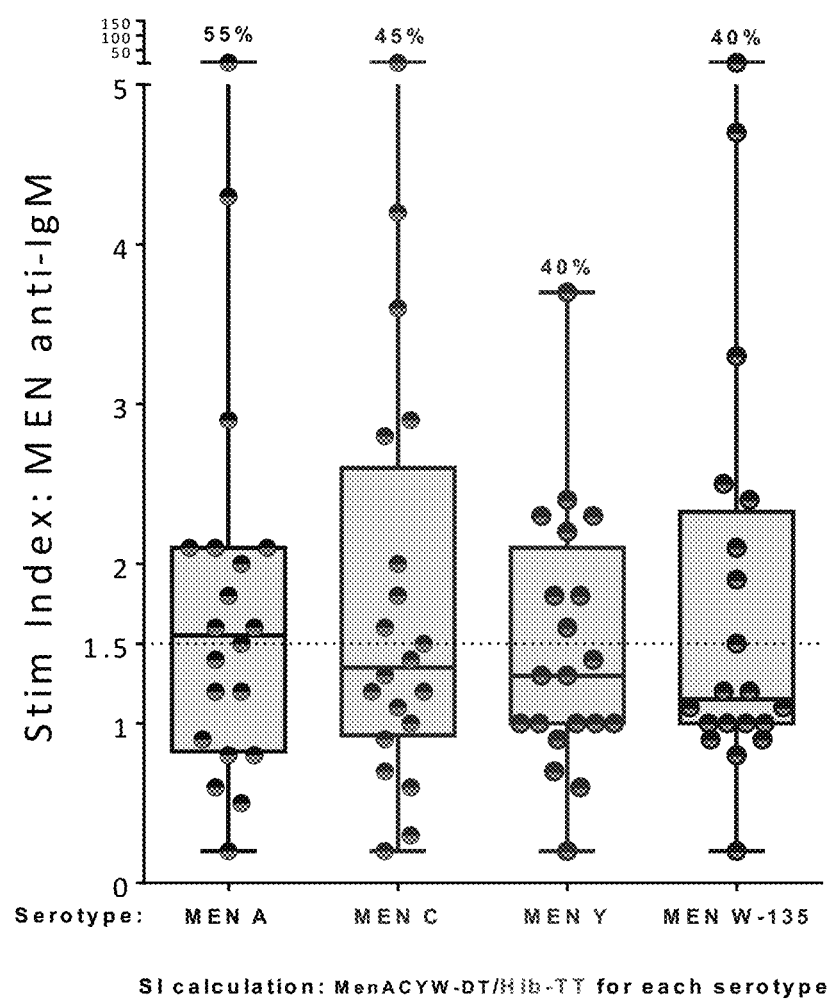

The analysis demonstrated that MenACYW-DT-induced antibody responses can be produced using the nMIMIC B cell/$T_{FH}$ model. As seen in FIG. 5, MenACYW-DT-induced antigen-specific IgM antibody responses to all four meningococcal serotypes (A, C, Y, W-135) were observed in several donors. Increased fold changes over background are shown in FIG. 5.

Figure 6A:
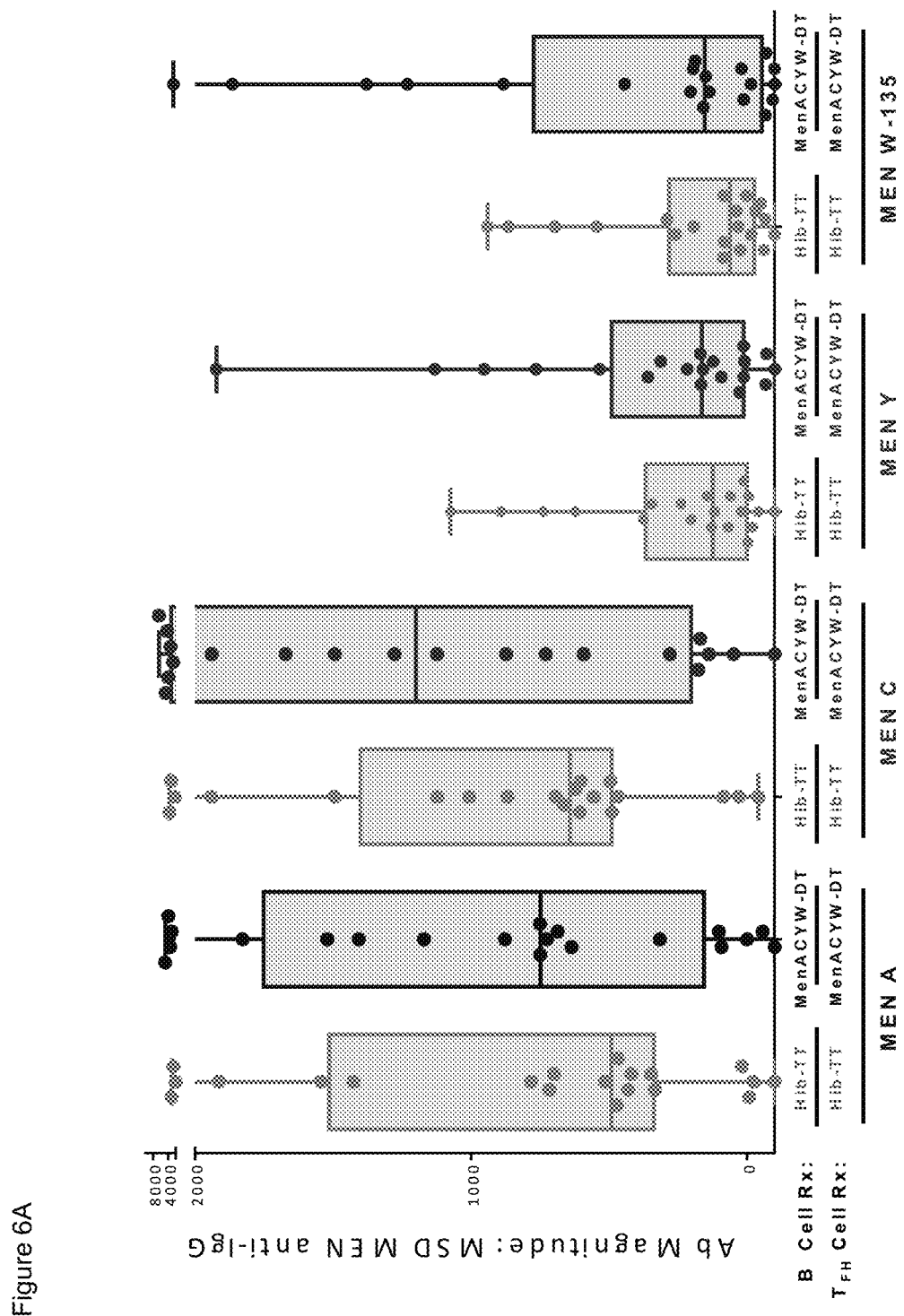
FIGS. 6A-6B. MenACYW-DT-induced IgG antibody responses were observed in the nMIMIC model. MenA-CYW-DT-induced antigen-specific IgG antibody responses in the nMIMIC to all four meningococcal serotypes (A, C, Y, W-135), with several donors showing increased fold changes over background for serotype C. In these experiments Hib-TT ("Hib") serves as an irrelevant non-meningococcal background control.
Figure 6B:
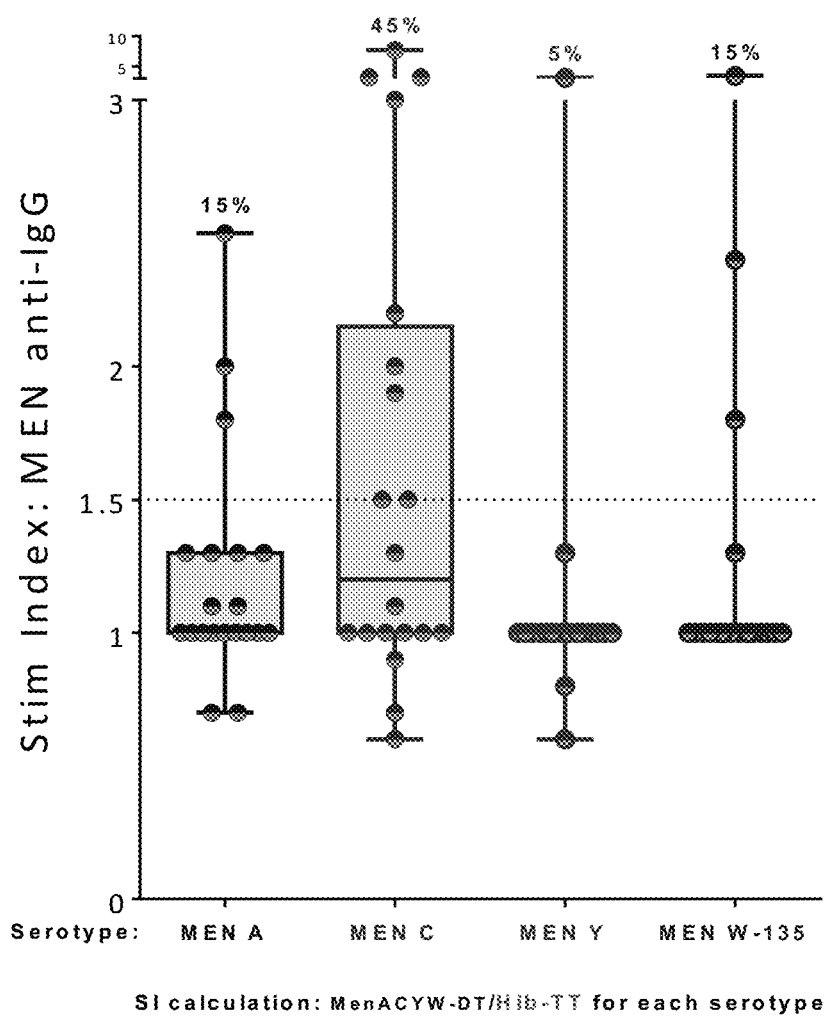

The results presented in FIG. 6 demonstrate that the nMIMIC B cell/$T_{FH}$ model can also be used to show MenACYW-DT-induced antigen-specific IgG antibody responses to each of the meningococcal serotypes, with several donors showing increased fold changes over background for serotype C.

nMIMIC B cell/$T_{FH}$ Cell Model—Dengue

Use of the nMIMIC B cell/$T_{FH}$ cell model is detailed below and shown schematically in FIG. 4.

On day 0 where human cord blood monocytes (CBMCs) were collected and between $1\times10^6$ and $50\times10^6$ cells in a serum-free culture media were plated in wells of a 24-well culture plate. A first group of wells was treated with a $T_{FH}$ differentiation cocktail containing: a selected antigen (concentration optimized for the selected antigen), anti-CD28 antibodies (0.1 µg/ml to 10 µg/ml), IL-6 (1 ng/ml to 500 ng/ml), and IL-12 (1 to 500 ng/ml); a second group of wells was left untreated to serve as feeder cells in later steps; a third group of cells was left untreated to serve as a negative control. The selected vaccines were the Dengue Fever Virus vaccine consisting of serotypes 1, 2, 3, and 4 (Sanofi Pasteur) and Hib-TT (control).

On day 3, CBMCs were harvested from selected wells by vigorous pipetting and/or gentle scraping of cells into conical tubes, followed by a rinse with a serum-free culture media. CD4+ T cells were isolated from the harvested CBMC using negative selection by magnetic bead isolation. The CD4+ T cells were then plated in a serum-free culture media at a concentration of $1\times10^5$ and $10\times10^6$ cells per well in 96-well culture plates. Between $1\times10^4$ and $5\times10^5$ irradiated CBMC feeder cells and, additional $T_{FH}$ differentiation cocktail was added to selected wells.

On day 6, additional irradiated feeder cells ($1\times10^3$ to $1\times10^5$) and additional $T_{FH}$ differentiation cocktail was added to selected wells.

On day 10, $T_{FH}$ were harvested from the wells and between $1\times10^4$ and $5\times10^5$ cells were co-cultured with $1\times10^5$ to $10\times10^6$ isolated cord blood B cells (negative magnetic bead selection) in a hydrogel for 3D cell culture. A range of between 1:1 and 1:100 $T_{FH}$ cell to B cell co-culture ratio was prepared. The same antigen that was present in the $T_{FH}$ differentiation cocktail was added to the $T_{FH}$ cell/B cells co-culture.

On day 12, IL-21 was added (1 to 500 ng/ml) to the $T_{FH}$ cell/B cell co-culture. On day 14, IL-21 was again added to the $T_{FH}$ cell/B cell co-culture.

On day 20, B cells were harvested from the culture and culture media was collected. IgM and IgG antigen-specific antibody production was analyzed using Meso Scale Discovery 96-well plates coated with all four Dengue Virus serotype antigens (1, 2, 3, and 4). MSDs IgM and IgG secondary antibodies were used to detect antibodies in supernatants.

Figure 7:
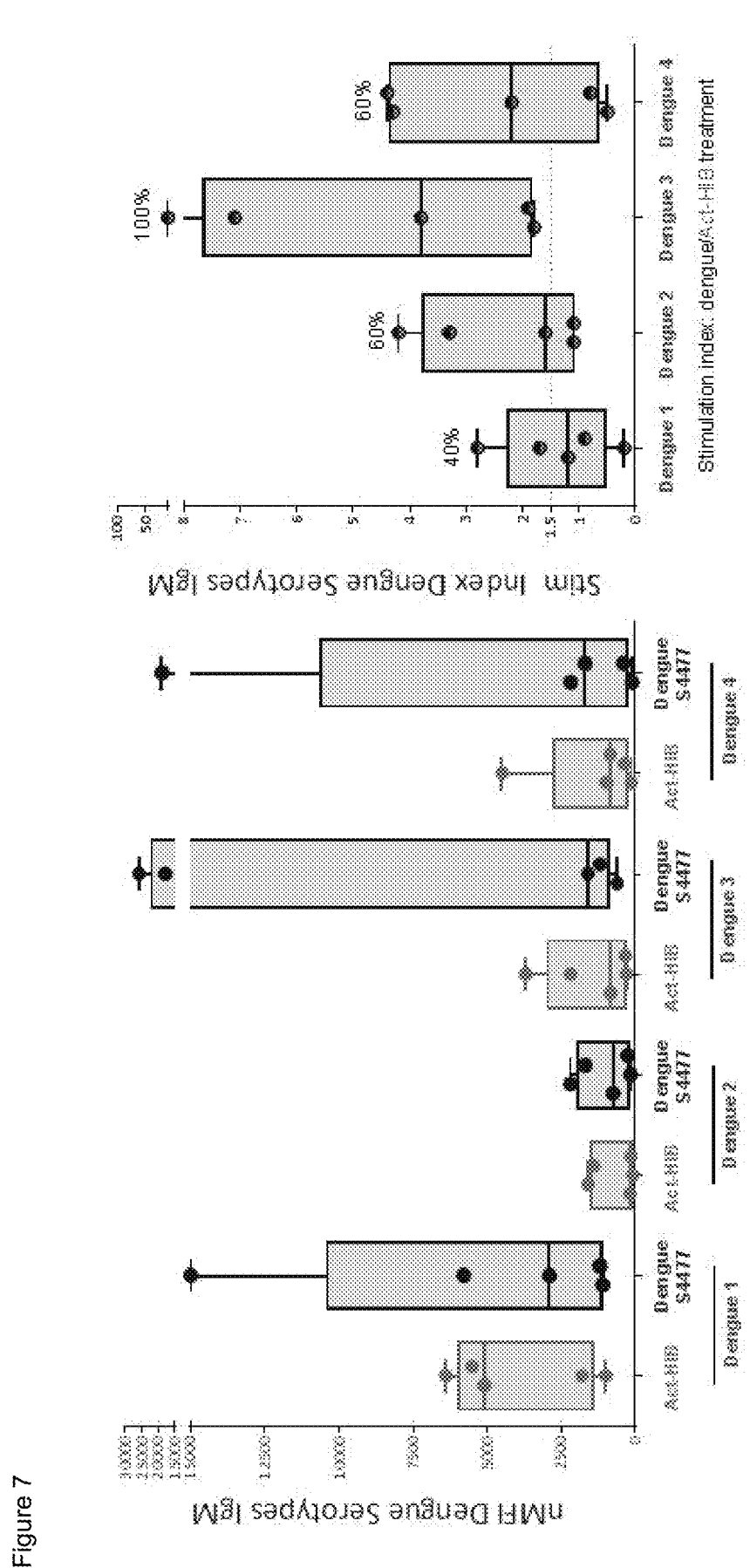
FIG. 7. Dengue Virus vaccine-induced IgM antibody responses were observed in the nMIMIC model. Dengue vaccine-induced antigen-specific IgM antibody responses in the nMIMIC model to all four Dengue vaccine serotypes (1, 2, 3, 4), with several donors showing increased fold changes over background for serotype 1, 3 and 4. In these experiments Act Hib-TT ("Act Hib") serves as an irrelevant non-Dengue virus background control. Antibody magnitude is shown on the left of the graph and stimulation index on the right of the graph. The stimulation index (SI) was calculated by dividing dengue antibody responses over Act-HIB control. An SI equal to or greater than 1.5 is considered a positive response.

The analysis demonstrated that Dengue Virus-induced antibody responses can be produced using the nMIMIC B cell/$T_{FH}$ model. As seen in FIG. 7, Dengue Virus-induced antigen-specific IgM antibody responses to all four Dengue serotypes (1, 2, 3, and 4) were observed in several donors. Increased fold changes over background are shown in FIG. 7.

The results presented in FIG. 7 demonstrate that the nMIMIC B cell/$T_{FH}$ model can also be used to show Dengue Virus-induced antigen-specific IgM antibody responses to each of the Dengue serotypes, with several donors showing increased fold changes over background for serotypes.

nMIMIC B cell/$T_{FH}$ Cell Model—Yellow Fever Vaccine

Use of the nMIMIC B cell/$T_{FH}$ cell model is detailed below and shown schematically in FIG. 4.

On day 0 where human cord blood monocytes (CBMCs) were collected and between $1\times10^6$ and $50\times10^6$ cells in a serum-free culture media were plated in wells of a 24-well culture plate. A first group of wells was treated with a $T_{FH}$ differentiation cocktail containing: a selected antigen (concentration optimized for the selected antigen), anti-CD28 antibodies (0.1 µg/ml to 10 µg/ml), IL-6 (1 ng/ml to 500 ng/ml), and IL-12 (1 ng/ml to 500 ng/ml); a second group of wells was left untreated to serve as feeder cells in later steps; a third group of cells was left untreated to serve as a negative control. The selected vaccine was a 17D Yellow fever virus vaccine (Sanofi Pasteur) and a Dengue Vaccine (control).

On day 3, CBMCs were harvested from selected wells by vigorous pipetting and/or scraping cells into conical tubes, followed by a rinse with a serum-free culture media. CD4+ T cells were isolated from the harvested CBMC using negative selection by magnetic bead isolation. The CD4+ T cells were then plated in a serum-free culture media at a concentration of $1\times10^5$ and $10\times10^6$ cells per well in 96-well culture plates. Between $1\times10^4$ and $5\times10^5$ irradiated CBMC feeder cells and additional $T_{FH}$ differentiation cocktail was added to selected wells.

On day 6, additional irradiated feeder cells ($1\times10^3$ to $1\times10^5$) and additional $T_{FH}$ differentiation cocktail was added to selected wells.

On day 10, $T_{FH}$ were harvested from the wells and between $1\times10^4$ and $5\times10^5$ cells were co-cultured with $1\times10^5$ to $10\times10^6$ isolated cord blood B cells (negative magnetic bead selection) in a hydrogel for 3D cell culture. A range of between 1:1 and 1:100 $T_{FH}$ cell to B cell co-culture ratio was prepared. The same antigen that was present in the $T_{FH}$ differentiation cocktail was added to the $T_{FH}$ cell/B cells co-culture.

On day 12, IL-21 was added (1 ng/ml to 500 ng/ml) to the $T_{FH}$ cell/B cell co-culture. On day 14, IL-21 was again added to the $T_{FH}$ cell/B cell co-culture.

On day 20, B cells were harvest from the culture and culture media was collected. IgM and IgG antigen-specific antibody production was analyzed using Meso Scale Discovery 96-well plates coated with 17D Yellow fever virus vaccine. MSDs IgM and IgG secondary antibodies were used to detect antibodies in supernatants.

Figure 8:
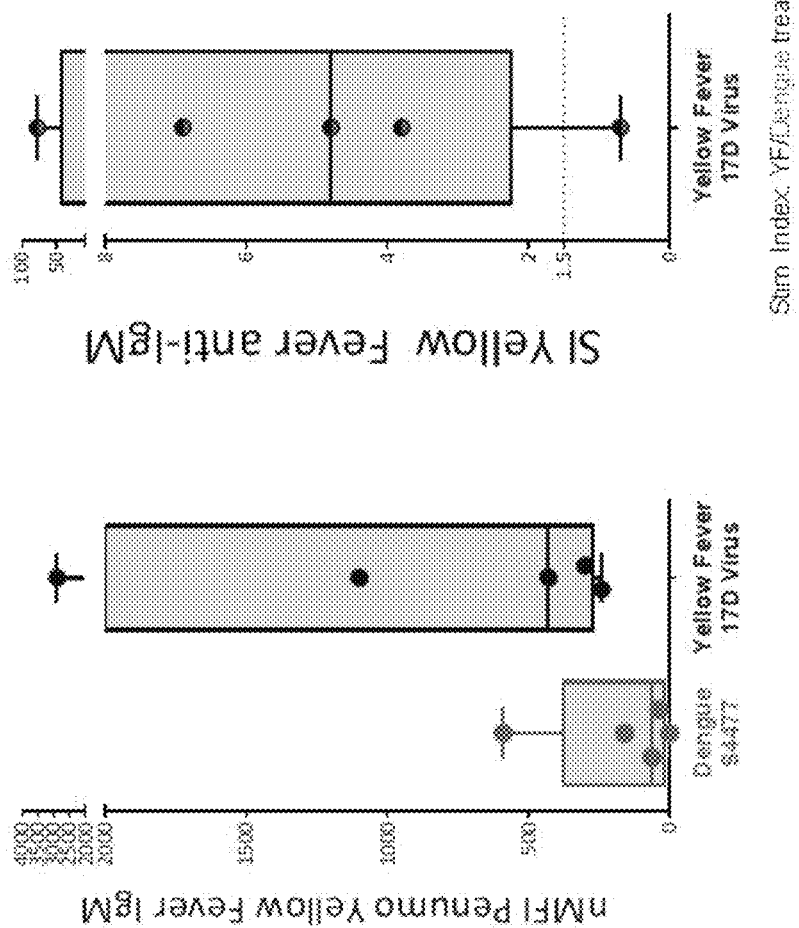
FIG. 8. Yellow Fever Virus vaccine-induced IgG antibody responses were observed in the nMIMIC model. Yellow Fever vaccine-induced antigen-specific IgM antibody responses in the nMIMIC model to the 17D Yellow fever virus vaccine, with several donors showing increased fold changes over background. In these experiments Dengue virus ("Dengue") serves as an irrelevant non-Yellow Fever virus background control. Antibody magnitude is shown on the left of the graph and stimulation index on the right of the graph. The stimulation index (SI) was calculated by dividing Yellow Fever antibody responses over Dengue Fever control. An SI equal to or greater than 1.5 is considered a positive response.

The analysis demonstrated that the 17D Yellow fever virus vaccine-induced antibody responses can be produced using the nMIMIC B cell/$T_{FH}$ model. As seen in FIG. 8, the 17D Yellow fever virus vaccine-induced antigen-specific IgM antibody responses were observed in several donors. Increased fold changes over background are shown in FIG. 8 to the right.

The results presented in FIG. 8 demonstrate that the nMIMIC B cell/$T_{FH}$ model can also be used to show the 17D Yellow fever virus vaccine-induced antigen-specific IgM antibody responses to the vaccine, with several donors showing increased fold changes over background.

nMIMIC B Cell/$T_{FH}$ Cell Model—Meningococcal Vaccine

Use of the nMIMIC B cell/$T_{FH}$ cell model is detailed below and shown schematically in FIG. 4.

On day 0 where human cord blood monocytes (CBMCs) were collected and between $1 \times 10^6$ and $50 \times 10^6$ cells in a serum-free culture media were plated in wells of a 24-well culture plate. A first group of wells was treated with a $T_{FH}$ differentiation cocktail containing: a selected antigen (concentration optimized for the selected antigen), anti-CD28 antibodies (0.1 µg/ml to 10 µg/ml), IL-6 (1 ng/ml to 500 ng/ml), and IL-12 (1 ng/ml to 500 ng/ml); a second group of wells was left untreated to serve as feeder cells in later steps; a third group of cells was left untreated to serve as a negative control. The selected vaccines were a meningococcal polysaccharide groups A, C, Y and W-135 diphtheria conjugate vaccine (MenACYW-DT) and groups A, C, Y and W-135 tetanus toxoid conjugate vaccine and Hib-TT (control).

On day 3, CBMCs were harvested from selected wells by vigorous pipetting and/or scraping cells into conical tubes, followed by a rinse with a serum-free culture media. CD4+ T cells were isolated from the harvested CBMC using negative selection by magnetic bead isolation. The CD4+ T cells were then plated in a serum-free culture media at a concentration of $1 \times 10^5$ and $10 \times 10^6$ cells per well in 96-well culture plates. Between $1 \times 10^4$ and $5 \times 10^5$ irradiated CBMC feeder cells and additional $T_{FH}$ differentiation cocktail was added to selected wells.

On day 6, additional irradiated feeder cells ($1 \times 10^3$ to $1 \times 10^5$) and additional $T_{FH}$ differentiation cocktail was added to selected wells.

On day 10, $T_{FH}$ were harvested from the wells and between $1 \times 10^4$ and $5 \times 10^5$ cells were co-cultured with $1 \times 10^5$ to $10 \times 10^6$ isolated cord blood B cells (negative magnetic bead selection) in a hydrogel for 3D cell culture. A range of between 1:1 and 1:100 $T_{FH}$ cell to B cell co-culture ratio was prepared. The same antigen that was present in the $T_{FH}$ differentiation cocktail was added to the $T_{FH}$ cell/B cells co-culture.

On day 12, IL-21 was added (1 ng/ml to 500 ng/ml) to the $T_{FH}$ cell/B cell co-culture. On day 14, IL-21 was again added to the $T_{FH}$ cell/B cell co-culture.

On day 20, B cells were harvest from the culture and culture media was collected. IgM and IgG antigen-specific antibody production was analyzed using Meso Scale Discovery 96-well plates coated with all four meningococcal serotype antigens (A, C, Y, W-135). MSDs IgM and IgG secondary antibodies were used to detect antibodies in supernatants.

Figure 9:
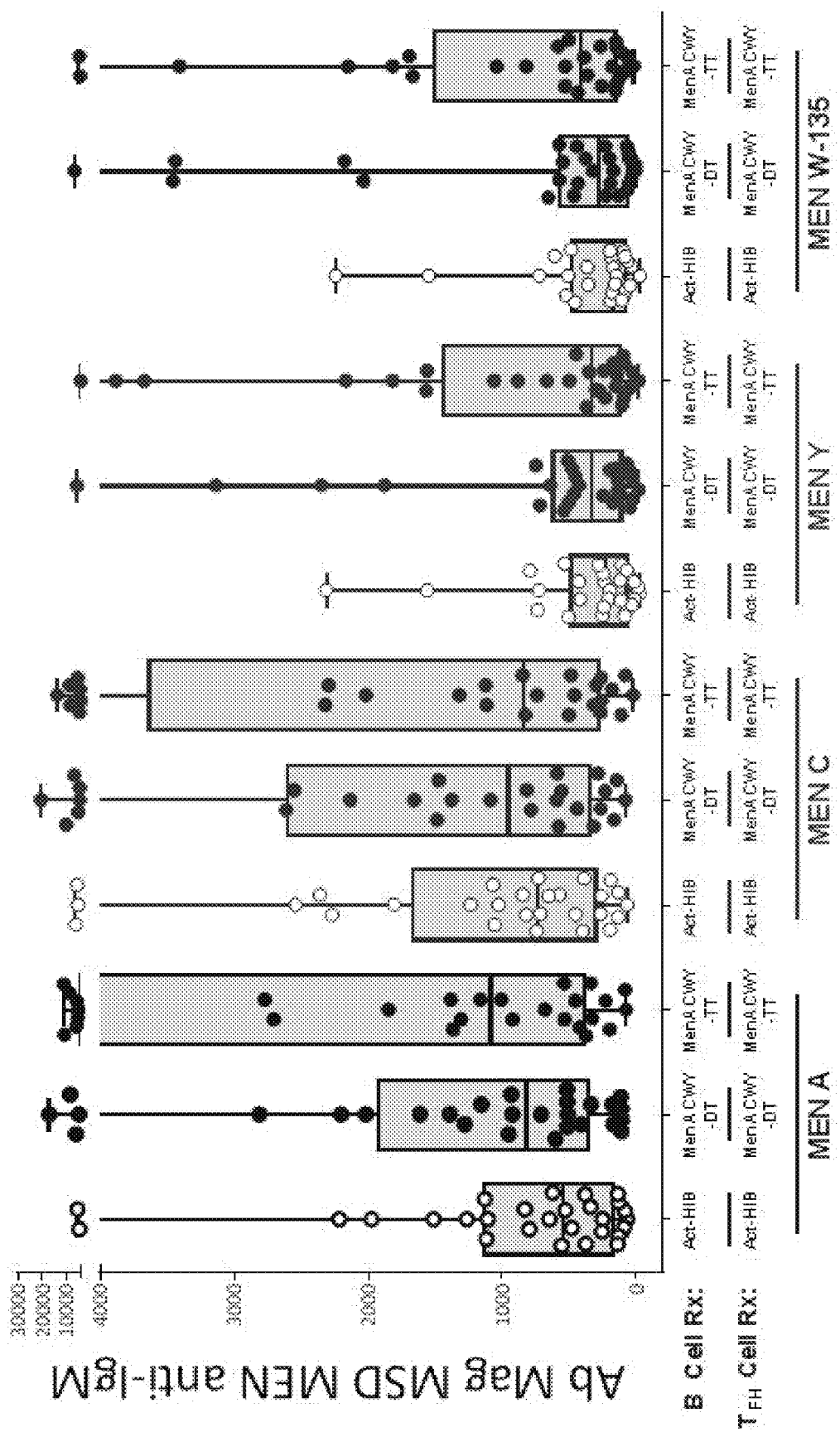
FIG. 9. Men ACWY-DT and ACWY-TT both stimulate meningococcal anti-IgM antibody production of all four serotypes: Ab magnitude. Meningococcal vaccine-induced IgM antibody responses were observed in the nMIMIC model. Both vaccines show positive IgM antibody responses of cord blood donors in the nMIMIC over our irrelevant non-meningococcal Act-HIB control.
Figure 10:
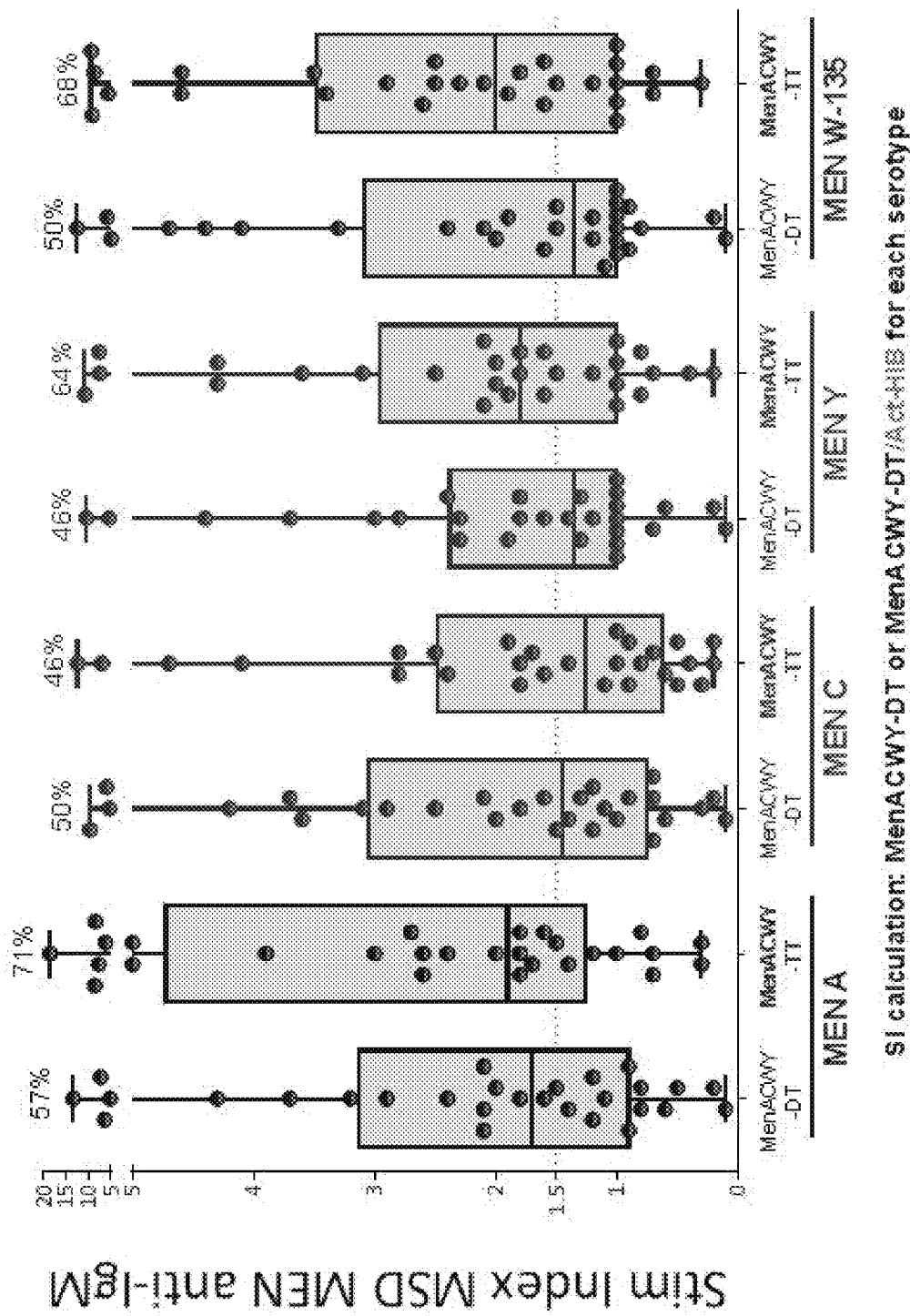
FIG. 10. Men ACWY-DT and ACWY-TT both stimulate meningococcal anti-IgM antibody production of all four serotypes: Stim Index. Meningococcal ACWY-DT and ACWY-TT stimulation index of IgM data are presented. An SI equal to or greater than 1.5 is considered a positive response. Percent, %, refers to number of donors that had an SI 1.5 or greater.

The analysis demonstrated that MenACYW-DT and TT induced antibody responses can be produced using the nMIMIC B cell/$T_{FH}$ model. As seen in FIG. 9, MenACYW-DT and TT induced antigen-specific IgM antibody responses to all four meningococcal serotypes (A, C, Y, W-135) were observed in several donors. Increased, fold changes over background are shown in FIG. 9. FIG. 10 also demonstrates that these vaccines also showed a stimulation index (SI) of greater than 1.5 for most serotypes for the IgM antibodies.

Figure 11:
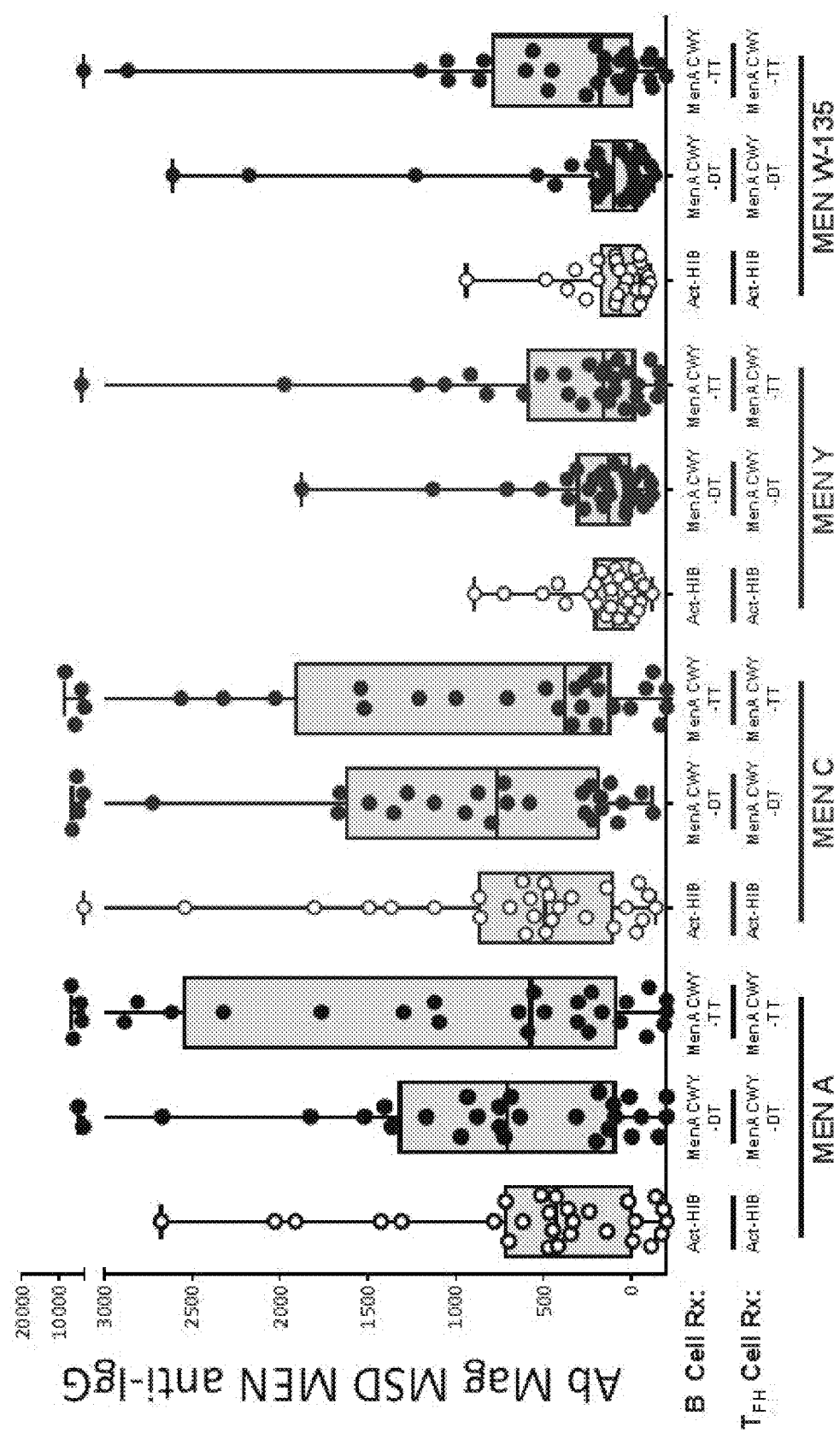
FIG. 11. Men ACWY-DT and ACWY-TI both stimulate meningococcal anti-IgG antibody production of all four serotypes: Ab magnitude. Meningococcal vaccine-induced IgG antibody responses were observed in the nMIMIC model. Men ACWY-DT and ACWY-TT both show positive IgG antibody responses of cord blood donors in the nMIMIC over our irrelevant non-meningococcal Act-HIB control.
Figure 12:
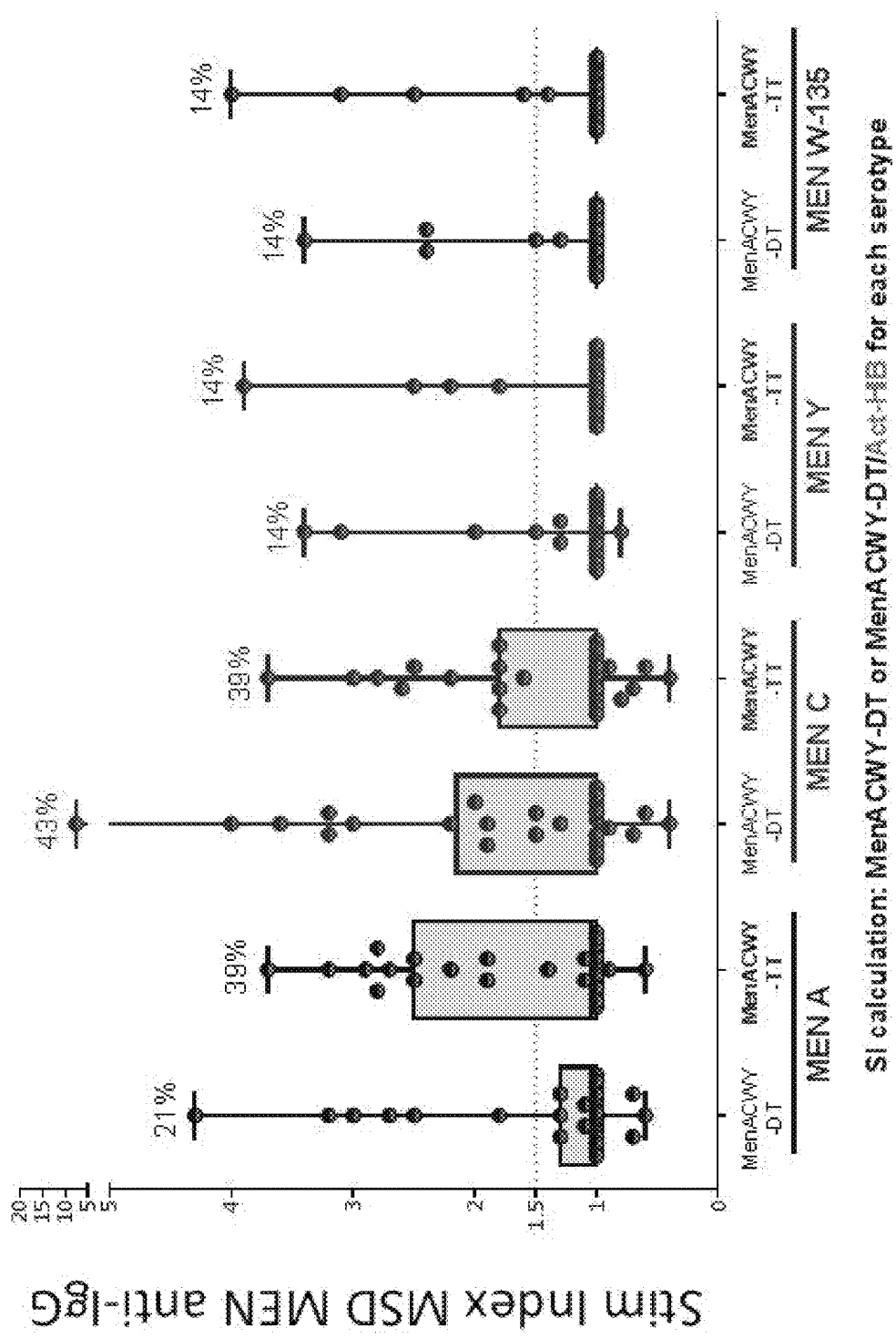
FIG. 12. Men ACWY-DT and ACWY-TT both stimulate meningococcal anti-IgM antibody production of all four serotypes: Stim Index. Meningococcal ACWY-DT and ACWY-TT stimulation index of IgG data are presented. An SI equal to or greater than 1.5 is considered a positive response. Percent, %, refers to number of donors that had an SI 1.5 or greater.

FIG. 11 shows all four serotypes of MenACYW-DT and TT both show positive antibody, IgG responses of cord blood donors in the nMIMIC over our irrelevant non-meningococcal Act-HIB control. FIG. 12 shows the Stimulation Index (SI) of IgG antibody data.

The results presented in FIG. 9-12 demonstrate that the nMIMIC B cell/$T_{FH}$ model can also be used to show MenACYW-DT and Men ACYW-TT vaccines induced antigen-specific IgG and IgM antibody responses to each of the meningococcal serotypes, with several donors showing increased fold changes over background.

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of screening a neonatal vaccine for activity comprising:
   (a) adding a neonatal vaccine and one or more cellular activator to a first in vitro cell culture comprising cord blood CD4+ T cells and maintaining the cell culture for about 8-12 days under conditions promoting development of vaccine-specific T follicular helper ($T_{FH}$) cells,
   wherein the cellular activators are one or more of an anti-CD28 antibody, IL-2, IL-6, IL-12, IL-21, and IL-23, and
   wherein irradiated feeder cells and additional vaccine are added on one of day 2, 3 or 4 after the initial vaccine addition, and on one of day 5, 6 or 7 after the initial vaccine addition;
   (b) forming a second in vitro cell culture comprising $T_{FH}$ cells developed in (a) and cord blood B cells,
   wherein the ratio of $T_{FH}$ cells to cord blood B cells in the second cell culture ranges from about 1:1 to about 1:100;
   (c) adding a vaccine-specific antigen to the cell culture of (b) and maintaining the culture for about 1-25 days under conditions promoting a cellular response; and
   (d) analyzing supernatant and/or cells from the cell culture of (c) for a cellular response, thereby screening a neonatal vaccine for activity.

2. The method of claim 1 wherein the irradiated feeder cells are cord blood mononuclear cells (CBMCs) grown in a serum-free culture media.

3. The method of claim 1 wherein the culture of (c) is maintained for about 8-12 days.

4. The method of claim 1 wherein IL-21 is added to the culture of (c).

5. The method of claim 1 wherein the culture of (c) is maintained for about 1-25 days and IL-21 is added upon addition of the vaccine-specific antigen to the second cell culture, on one of day 2, 3 or 4 after preparation of the second cell culture, and on one of day 5, 6 or 7 after preparation of the second cell culture.

6. The method of claim 5 wherein the neonatal vaccine is an inactivated, attenuated, toxoid, subunit, conjugate, valence and heterotypic vaccine, or a protein, peptide, polynucleotide, oligonucleotide, polysaccharide, virus, virion, bacteria, fungi, or fragment thereof, or antigen-primed DCs.

7. The method of claim 5 wherein the vaccine-specific antigen is a portion of the neonatal vaccine or a component of the neonatal vaccine.

8. The method of claim 5 wherein the cord blood B cells are autologous to the cord blood CD4+ T cells.

9. The method of claim 5 wherein the cord blood B cells are treated with CpG2006 prior to addition of the cord blood B cells to the second cell culture.

10. The method of claim 5 wherein the second cell culture is formed in a three-dimensional matrix.

11. The method of claim 10 wherein the matrix is a gel matrix.

12. The method of claim 1 wherein the cellular response is one or more of production of a cytokine by the $T_{FH}$ cells, expression of a marker by the $T_{FH}$ cells, production of a cytokine by the B cells, expression of a marker by the B cells, and production of an antibody with binding specificity for the vaccine-specific antigen by the B cells.

13. The method of claim 12 wherein the cytokine is one or more of CXCL13, TNFα, IFNγ, IL-2, IL-4, IL-6, IL-8, IL-10, IL-13, IL-17, or IL-21.

14. The method of claim 12 wherein the marker is one or more of CD10, CD19, CD20, CD24, CD27, CD38, CD40, CD86, CD138, IgD, IgG, and IgM.

15. A method of assessing efficacy of a neonatal vaccine comprising:
(a) adding a neonatal vaccine and one or more cellular activator to a first in vitro cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 or 4 after the initial vaccine addition, and on one of day 5, 6 or 7 after the initial vaccine addition;
(b) forming a second in vitro cell culture comprising $T_{FH}$ cells developed in (a) and cord blood B cells,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response; and
(d) analyzing supernatant and/or cells from the cell culture of (c) for a cellular response, thereby assessing efficacy of a neonatal vaccine.

16. A method of predicting in vivo efficacy of a neonatal vaccine using an in vitro cell culture comprising:
(a) adding a vaccine and one or more cellular activator to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 or 4 after the initial vaccine addition, and on one of day 5, 6 or 7 after the initial vaccine addition;
(b) forming a second cell culture comprising $T_{FH}$ cells developed in (a) and cord blood B cells,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response, and
(d) analyzing supernatant and/or cells from the cell culture of (c) for a cellular response, wherein when a cellular response is found the neonatal vaccine is predicted to have in vivo efficacy.

17. A method of screening a neonatal vaccine for activity comprising:
(a) adding a neonatal vaccine and cellular activators to a first cell culture comprising cord blood CD4+ T cells and maintaining the cell culture for about 8-12 days under conditions promoting development of vaccine-specific T follicular helper ($T_{FH}$) cells,
wherein the cellular activators are one or more of an anti-CD28 antibody, IL-2, IL-6, IL-12, IL-21, and IL-23, and
wherein irradiated feeder cells and additional vaccine are added on one of day 2, 3 or 4 after the initial vaccine addition, and on one of day 5, 6 or 7 after the initial vaccine addition;
(b) forming a second cell culture comprising $T_{FH}$ cells developed in (a) and autologous cord blood B cells in a three-dimensional matrix,
wherein the ratio of $T_{FH}$ cells to cord blood B cells in the second cell culture ranges from about 1:1 to about 1:100;
(c) adding a vaccine-specific antigen to the cell culture of (b) and maintaining the culture for about 1-25 days under conditions promoting a cellular response,
wherein IL-21 is added to the cell culture of (b) upon addition of the antigen, on one of day 2, 3 or 4 after preparation of the second cell culture, and on one of day 5, 6 or 7 after preparation of the second cell culture; and
(d) analyzing supernatant and/or cells from the cell culture of (c) for production of an antibody with binding specificity for the vaccine-specific antigen by the B cells, thereby screening a neonatal vaccine for activity.

18. The method of claim 17 wherein the irradiated feeder cells are cord blood mononuclear cells (CBMCs) grown in a serum-free culture media.

19. The method of claim 17 wherein the neonatal vaccine is an inactivated, attenuated, toxoid, subunit, conjugate, valence and heterotypic vaccine, or a protein, peptide, polynucleotide, oligonucleotide, polysaccharide, virus, virion, bacteria, fungi, or fragment thereof, or antigen-primed DCs.

20. The method of claim 17 wherein the vaccine-specific antigen is a portion of the neonatal vaccine or a component of the neonatal vaccine.

21. The method of claim 17 wherein the cord blood B cells are treated with CpG2006 prior to addition of the cord blood B cells to the second cell culture.

22. The method of claim 17 wherein the matrix is a gel matrix.

23. A method of assessing efficacy of a neonatal vaccine comprising:
(a) adding a neontal vaccine and cellular activators to a first cell culture comprising cord blood CD4+ T cells and maintaining the cell culture for about 8-12 days under conditions promoting development of vaccine-specific T follicular helper ($T_{FH}$) cells, wherein the cellular activators are one or more of an anti-CD28 antibody, IL-2, IL-6, IL-12, IL-21, and IL-23, and wherein irradiated feeder cells and additional vaccine are added on one of day 2, 3 or 4 after the initial vaccine addition, and on one of day 5, 6 or 7 after the initial vaccine addition;

(b) forming a second cell culture comprising $T_{FH}$ cells developed in (a) and autologous cord blood B cells in a three-dimensional matrix, wherein the ratio of $T_{FH}$ cells to cord blood B cells in the second cell culture ranges from about 1:1 to about 1:100;

(c) adding a vaccine-specific antigen to the cell culture of (b) and maintaining the culture for about 1-25 days under conditions promoting a cellular response, wherein IL-21 is added to the cell culture of (b) upon addition of the antigen, on one of day 2, 3 or 4 after preparation of the second cell culture, and on one of day 5, 6 or 7 after preparation of the second cell culture; and (d) analyzing supernatant and/or cells from the cell culture of (c) for production of an antibody with binding specificity for the vaccine-specific antigen by the B cells, thereby assessing efficacy of a neonatal vaccine.

24. A method of predicting in vivo efficacy of a neonatal vaccine using an in vitro cell culture comprising:

(a) adding a neontal vaccine and cellular activators to a first cell culture comprising cord blood CD4+ T cells and maintaining the cell culture for about 8-12 days under conditions promoting development of vaccine-specific T follicular helper ($T_{FH}$) cells, wherein the cellular activators are one or more of an anti-CD28 antibody, IL-2, IL-6, IL-12, IL-21, and IL-23, and wherein irradiated feeder cells and additional vaccine are added on one of day 2, 3 or 4 after the initial vaccine addition, and on one of day 5, 6 or 7 after the initial vaccine addition;

(b) forming a second cell culture comprising $T_{FH}$ cells developed in (a) and autologous cord blood B cells in a three-dimensional matrix, wherein the ratio of $T_{FH}$ cells to cord blood B cells in the second cell culture ranges from about 1:1 to about 1:100;

(c) adding a vaccine-specific antigen to the cell culture of (b) and maintaining the culture for about 1-25 days under conditions promoting a cellular response, wherein IL-21 is added to the cell culture of (b) upon addition of the antigen, on one of day 2, 3 or 4 after preparation of the second cell culture, and on one of day 5, 6 or 7 after preparation of the second cell culture; and (d) analyzing supernatant and/or cells from the cell culture of (c) for production of an antibody with binding specificity for the vaccine-specific antigen by the B cells, wherein when such antibody is found the neonatal vaccine is predicted to have in vivo efficacy.

* * * * *